United States Patent
Kobayashi et al.

(10) Patent No.: US 8,679,023 B2
(45) Date of Patent: Mar. 25, 2014

(54) TISSUE INSERTION TYPE ULTRASONIC PROBE

(75) Inventors: Hidemitsu Kobayashi, Mitaka (JP); Noriaki Tan, Mitaka (JP); Kazutoshi Tsuchida, Mitaka (JP); Hiroaki Wakabayashi, Mitaka (JP); Shigeyuki Hirukawa, Mitaka (JP)

(73) Assignee: Hitachi Aloka Medical, Ltd., Tokyo (JP)

( * ) Notice: Subject to any disclaimer, the term of this patent is extended or adjusted under 35 U.S.C. 154(b) by 0 days.

(21) Appl. No.: 13/273,868

(22) Filed: Oct. 14, 2011

(65) Prior Publication Data

US 2012/0108978 A1 May 3, 2012

(30) Foreign Application Priority Data

Oct. 28, 2010 (JP) ................. 2010-241908

(51) Int. Cl.
*A61B 8/14* (2006.01)

(52) U.S. Cl.
USPC .......................... 600/459; 600/437

(58) Field of Classification Search
USPC ................ 600/437–469
See application file for complete search history.

(56) References Cited

U.S. PATENT DOCUMENTS

| | | | |
|---|---|---|---|
| 3,978,865 A * | 9/1976 | Trabucco | 607/9 |
| 4,793,326 A | 12/1988 | Shishido | |
| 5,314,461 A * | 5/1994 | Borghi | 607/127 |
| 5,374,285 A * | 12/1994 | Vaiani et al. | 607/117 |
| 5,471,988 A | 12/1995 | Fujio et al. | |
| 5,551,426 A * | 9/1996 | Hummel et al. | 600/374 |
| 5,735,792 A * | 4/1998 | Vanden Hoek et al. | 600/138 |
| 5,738,100 A * | 4/1998 | Yagami et al. | 600/466 |
| 6,579,244 B2 | 6/2003 | Goodwin | |
| 2004/0204670 A1 | 10/2004 | Nita et al. | |
| 2005/0107816 A1 | 5/2005 | Pingleton et al. | |
| 2005/0113688 A1 | 5/2005 | Nita et al. | |

(Continued)

FOREIGN PATENT DOCUMENTS

| | | |
|---|---|---|
| WO | 01/49227 A1 | 7/2001 |
| WO | 2009/152244 A1 | 12/2009 |
| WO | 2010/048208 A1 | 4/2010 |
| WO | 2010/129773 A1 | 11/2010 |

OTHER PUBLICATIONS

European Search Report dated Feb. 28, 2012, issued in corresponding European Patent Application No. 11008413.4, (11 pages).

(Continued)

*Primary Examiner* — Sanjay Cattungal
(74) *Attorney, Agent, or Firm* — Westerman, Hattori, Daniels & Adrian, LLP

(57) ABSTRACT

There is provided an ultrasonic probe for supporting spine surgery which can execute both inspection by tactile sense and inspection by ultrasound diagnosis. A front-end component provided at a front end of an insertion unit. The front-end component comprises a metal component and a resin component, and the metal component comprises a tactile member and an anchor. The resin component comprises a cap portion and a surrounding portion. An insertion portion in the front-end component is inserted into a front end portion of a pipe. The anchor and the front end portion are in close proximity with a certain distance therebetween, such that insulation is secured and vibration transmitted from a head can be transmitted from the anchor to the pipe in a superior manner.

13 Claims, 17 Drawing Sheets

(56) References Cited

U.S. PATENT DOCUMENTS

| | | |
|---|---|---|
| 2008/0208121 A1 | 8/2008 | Youssef et al. |
| 2010/0201796 A1 | 8/2010 | Chan |
| 2011/0077525 A1* | 3/2011 | Baraso et al. ............... 600/459 |
| 2011/0208062 A1* | 8/2011 | Baraso et al. ............... 600/459 |

OTHER PUBLICATIONS

Chinese Office Action dated Aug. 23, 2013, issued in corresponding Chinese Patent Application No. 201110342605.5, w/English translation.

* cited by examiner

TISSUE INSERTION TYPE ULTRASONIC PROBE

BACKGROUND

1. Technical Field

The present invention relates to a tissue insertion type ultrasonic probe, and in particular, to an ultrasonic probe used for inspection of a guide hole formed in a vertebral bone in spine surgery.

2. Background Art

An ultrasound diagnostic apparatus is an apparatus which forms an ultrasound image based on a reception signal obtained by transmission and reception of ultrasound to and from a tissue of a living body. The ultrasound diagnostic apparatus comprises a device body and an ultrasonic probe. The device body comprises a transmission unit, a reception unit, an image formation unit, a display, an operation panel, or the like, and the ultrasonic probe is detachably attached on the device body. The ultrasonic probe generally comprises an array transducer. The array transducer comprises a plurality of transducer elements which are aligned, and an ultrasound beam is formed by the plurality of transducer elements. A beam scanning plane is formed by electronic scanning of the ultrasound beam. The device body forms a two-dimensional tomographic image (B mode image) corresponding to the beam scanning plane based on a reception signal which is output from the ultrasonic probe. As the ultrasound image, in addition to the two-dimensional tomographic image, there are also known a two-dimensional bloodstream image, a Doppler image, a three-dimensional image, or the like.

A surgery method of fixing a plurality of vertebral bones forming the spine using metal components is used more and more widely, and is illustrated in FIG. 1. The spine comprises a plurality of vertebral bones 10 and 12. An intervertebral disk 14 is present between the vertebral bones 10 and 12. Two bolts (or screws) 16 and 18 are mounted on each of the vertebral bones 10 and 12; that is, in the configuration shown in FIG. 1, a total of four bolts are mounted. Two bolts 16 and 18 arranged on the right side of each of the vertebral bones 10 and 12 are connected by a metal rod 20. Similarly, two bolts (not shown) arranged on the left side of each of the vertebral bones 10 and 12 are connected by another metal rod. With such a method, a positional relationship between the two vertebral bones 10 and 12 is fixed.

In the above-described fixing method, before the two bolts are mounted on each vertebral bone, two guide holes (pilot holes) are formed in each vertebral bone. FIG. 2 shows the vertebral bone 10. The vertebral bone 10 comprises a vertebral body or centrum 22 and a vertebral arch 24. A vertebral foramen (spinal canal) 26 through which a nerve passes is formed in the vertebral bone 10. Two guide holes 28 and 30 must be formed at appropriate positions and with appropriate angles. In particular, entrance or approaching of the guide holes 28 and 30 to the vertebral foramen 26 must be avoided. If the bolt is mounted in such an inappropriate guide hole, the nerve passing through the vertebral foramen 26 may be damaged. In consideration of such circumstances, the guide holes 28 and 30 are carefully formed using a surgery drill. However, in the process of forming the guide holes 28 and 30, it is not possible to see with human eyes the interior of the guide holes 28 and 30.

In view of this, in the related art, a metal tool dedicated for tactile inspection is repeatedly used in the formation process of the guide holes 28 and 30. The metal tool comprises a long-and-narrow wire-like shaft portion, and a slightly wide grip portion connected to the long-and-narrow shaft portion. A tactile tip (or feeler) having a small spherical shape is provided on a front end of the shaft portion. The shaft portion and the grip portion are integrated; that is, the metal tool is formed as a single metal member elongated along a straight line. The front end of the metal tool is inserted into the guide hole while the grip of the metal tool is held, and the inner wall surface of the guide hole is traced with the tactile tip. With such a process, the shape of the inner wall surface of the guide hole can be indirectly understood with the tactile sense. Specifically, the shape of the projections and depressions on the inner wall surface is transmitted to the grip portion as a movement (vibration) of the tactile tip. By feeling the vibration with a plurality of fingertips, a user can indirectly understand the shape of the projections and depressions of the inner wall surface.

However, in the above-described inspection method with tactile sense using the metal tool, the state of the guide hole is not necessarily evaluated sufficiently. With the tactile sense method, a minute crack cannot be identified, and the inside of the guide hole cannot be observed. Even if the inspection by the tactile sense itself does not have any problem, inspection of the state of the guide hole (or structure of the vertebral bone) with a method other than the tactile sense is desired, from the viewpoint of further improving safety. In consideration of the above, realization of a tissue insertion type ultrasonic probe which can execute both tactile inspection and ultrasound diagnosis is demanded. With such an ultrasonic probe, it is possible to execute the ultrasound diagnosis immediately after the tactile inspection, to execute the tactile inspection immediately after the ultrasound diagnosis, or to simultaneously execute the tactile inspection and the ultrasound diagnosis, without inserting or removing the insertion unit.

U.S. Pat. No. 6,579,244 discloses a system which executes ultrasound diagnosis by inserting a member, which transmits and receives ultrasound, into a pilot hole formed in a bone. However, this reference fails to disclose a probe which can execute both tactile inspection and ultrasound diagnosis. In addition, this reference fails to disclose a specific structure (array transducer, line, etc.) for forming a two-dimensional tomographic image.

In order to realize an ultrasonic probe for supporting spine surgery which can execute both the tactile inspection and ultrasound diagnosis, it is necessary to achieve both superior transmission of vibration and reliable insulation. In other words, from the viewpoint of reliable transmission of the vibration generated at the tactile member through the tube member and the operation unit to the hand of the user, the tactile member and the tube member are desirably formed with hard members (normally, metal members), and are directly connected. However, the transducer unit to which a voltage is applied is stored in the tube member, and the tube member may function as an electrical component when serving as a shielding member. Therefore, from the viewpoint of safety, the direct connection of the tube member and the tactile member is not desirable. Therefore, it is desired to reliably block the electrical conduction between the tube member and the tactile member while mechanically or physically firmly connecting the tube member and the tactile member.

SUMMARY

An advantage of the present invention is provision of a method of manufacturing an ultrasonic probe for supporting spine surgery which enables mechanically or physically firm connection of a tactile member and a tube member.

Another advantage of the present invention is provision of a method of manufacturing an ultrasonic probe for supporting spine surgery in which the array transducer is not affected by a heating process for connecting members.

According to one aspect of the present invention, there is provided an ultrasonic probe for supporting spine surgery, comprising an insertion unit which is inserted into a guide hole formed in a vertebral bone, and an operation unit which is connected to the insertion unit, to which vibration is transmitted from the insertion unit, and which is held by a user. The insertion unit comprises a tube member and a front-end component. The front-end component comprises an ultrasonic transducer which is provided at a front end portion of the tube member and is for inspecting an inside of the vertebral bone by ultrasound diagnosis, a metal member which is provided at the front end portion of the tube member and which has a tactile member for inspecting the inside of the vertebral bone with a tactile sense of the user and an anchor which is connected to the tactile member, and an insulating member having a surrounding portion surrounding the anchor. Of the front-end component, an insertion portion made of the anchor and the surrounding portion is fitted into the tube member.

With the above-described configuration, the inside of the tissue can be inspected with tactile sense by means of the ultrasonic probe, and the inside of the tissue can be inspected by ultrasound diagnosis (transmission and reception of ultrasound). More specifically, the tactile member can be contacted on the surface of the tissue and moved in various directions such as toward the front, rear, right, and left, so that the shape of the inside the tissue can be indirectly understood by means of the tactile sense. The vibration or force caused in the tactile member propagates through the tube member and is transmitted to the operation unit, and, further to a hand holding the operation unit. The ultrasound diagnosis by transmission and reception of ultrasound can be executed before, after, or simultaneously with the inspection using the tactile sense. Normally, a tomographic image is formed, and an image of the inside of the vertebral bone (for example, a surface layer of the guide hole) is formed. With the use of both the tactile judgment and visual judgment of the ultrasonic image, it is possible to evaluate whether or not the guide hole is appropriately formed. For example, because it is possible to evaluate structures up to the surface layer of the vertebral bone, it is possible to easily judge the state where the guide hole is close to the vertebral foramen. As the ultrasound diagnosis mode, desirably, a B mode is selected. Alternatively, other modes such as an A mode, a three-dimensional mode, a Doppler mode, or the like may be selected.

In the above-described configuration, the front-end component is formed with a metal member and an insulating member, and, in particular, of the metal member, the anchor is covered by a surrounding portion of an insulating member. Therefore, accidental contact of the metal member on the tube member can be effectively prevented. In addition, accidental contact of the metal member on the transducer unit can also be effectively prevented. Because the insertion portion in the front-end component is fitted to, or, desirably, pressurized into, the inside of the tube member, the front-end component and the tube member can be firmly connected mechanically to each other. In particular, in such a fitted state, of the metal member, the anchor is positioned inside the tube member, and, thus, the vibration can be effectively transmitted to the tube member existing around the anchor through the anchor positioned inside the tube member. The cap portion blocks a front end opening of the tube member, and prevents entrance of body fluid or the like into the tube member. The shape of the cap member may be set as a dome-shape swelling in the front direction, so that the safety to the living body can be improved.

A thickness of the surrounding portion around the anchor is desirably determined from the viewpoints of both insulation and vibration transmission. In general, from the viewpoint of insulation, the thickness is desirably thick, but from the viewpoint of the vibration transmission, the thickness is desirably thin. The shape of the anchor is desirably set as a shape extending in the axial direction of the tube member, and, in particular, is desirably set as a circular cylinder shape similar to the shape of the inside space of the tube member.

According to another aspect of the present invention, preferably, the insertion portion has a circular cylindrical shape, and the anchor has a circular cylindrical shape with a side surface having a detachment-preventing structure. When a simple circular cylinder shape is employed for the anchor, the anchor is easily detached. Therefore, the detachment-preventing structure is preferably formed on the side surface of the anchor as described. According to another aspect of the present invention, preferably, the detachment-preventing structure has at least one recess or projection. These shape elements cause unevenness in a direction perpendicular to the central axis.

According to another aspect of the present invention, preferably, the tube member is made of a metal pipe member having a shielding function and a vibration transmitting function, the insertion unit further comprises an insulating sheath tube covering an outer side of the tube member, the insulating member comprises a cap portion which is connected to the surrounding portion and which covers a front end opening of the tube member, and the cap portion and a front end opening of the insulating sheath tube are adhered to each other. The insulating sheath tube achieves protection of the tube member as the metal pipe member and, at the same time, protection of the living body, and electrically isolates the tube member from the living body. The cap portion and the insulating sheath tube may be formed from the same material or similar materials. The materials of the members are preferably determined such that at least the adhesion of the members is reliably executed.

According to another aspect of the present invention, preferably, the cap portion and the front end opening of the to insulating sheath tube are integrated by welding. With this configuration, the cap portion and the front end opening of the insulating sheath tube are completely sealed. With the use of welding, leakage of the adhesive from the insertion unit can be prevented.

According to another aspect of the present invention, preferably, the cap portion has a dome shape swelled in a front direction, and the tactile member has a shaft which protrudes from a central portion of the cap portion and which is directed in a predetermined direction perpendicular to a central axis of the tube member, and a spherical head provided at a front end portion of the shaft. As the tactile member, various forms may be considered. In any case, the tactile member is desirably formed so that the tactile member can naturally approach an inner wall surface of the guide hole, and can smoothly contact the surface of the bone. According to another aspect of the present invention, preferably, all or a part of the head protrudes toward a living body side in relation to a side surface level of the tube member in the predetermined direction. With such a configuration, the head can be reliably contacted with the inner wall surface of the guide hole.

According to another aspect of the present invention, preferably, the ultrasonic transducer is an array transducer comprising a plurality of transducer elements, an opening for allowing passage of ultrasound transmitted from or received by the array transducer in the predetermined direction is formed at the front end portion of the tube member, and a transducer unit comprising the array transducer is embedded at a deeper side of the opening in the tube member. According to another aspect of the present invention, preferably, an insulating molding is applied around the transducer unit.

According to another aspect of the present invention, there is provided a method of manufacturing an ultrasonic probe for supporting spine surgery, comprising the steps of manufacturing a front-end component comprising a metal member having a tactile member and an anchor connected to the tactile member, and an insulating member having a cap portion and a surrounding portion connected to the cap portion and surrounding the anchor; adhering the front-end component and an insulating sheath tube, to thereby manufacture an outer assembly by integrating the cap portion and an opening of the insulating sheath tube by welding; manufacturing an inner assembly by providing a transducer unit having an ultrasonic transducer in a front end portion of a metal pipe member; manufacturing an insertion unit by inserting the inner assembly into the outer assembly; and connecting the insertion unit and an operation unit.

With the above-described configuration, the outer assembly and the inner assembly are separately manufactured and then combined. Even if a heating process is executed for manufacturing the outer assembly, the inner assembly is not affected by the heat. With this configuration, the problem of polarization loss or the like of the array transducer can be prevented in advance. In the above-described configuration, the front-end component is first manufactured, and a gap between the anchor and the inner surface to of the metal pipe member at that point is defined as the shape and thickness of the surrounding portion. Therefore, even if a manufacturing error occurs in the later steps, insulation and superior vibration transmission can be secured. The front-end component and the insulating sheath tube are integrated by welding, and the inside of the outer assembly becomes a space completely closed in the front side. Therefore, even if a large amount of adhesive is applied to this space, the adhesive would not leak to the living body side.

According to another aspect of the present invention, preferably, in the step of manufacturing the outer assembly, a circular cylindrical slit is formed between an insertion portion in the front-end component and the insulating sheath tube, and, in the step of manufacturing the insertion unit, the front end portion of the metal pipe member is inserted into the circular cylindrical slit.

According to another aspect of the present invention, preferably, in the step of manufacturing the insertion unit, the inner assembly is positioned in the outer assembly such that a direction in which the tactile member points and a direction in which the ultrasonic transducer points match each other.

According to another aspect of the present invention, preferably, in the step of manufacturing the insertion unit, a molding adhesive is applied into the outer assembly before the inner assembly is inserted into the outer assembly.

DESCRIPTION OF EMBODIMENT

Preferred embodiments of the present invention will now be described with reference to the drawings.

Figure 1:
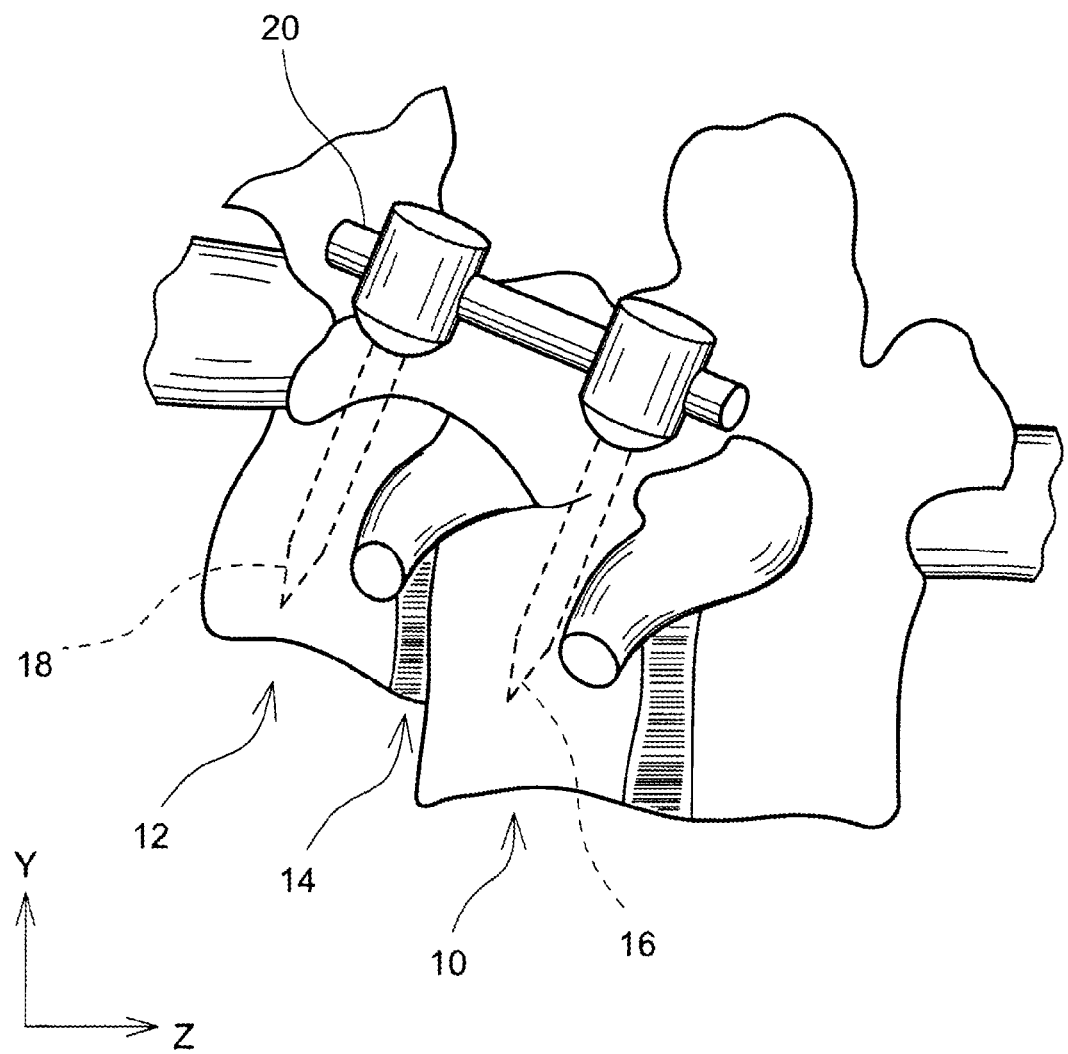
FIG. 1 is a diagram for explaining a spine fixing surgery using a metal tool.
Figure 2:
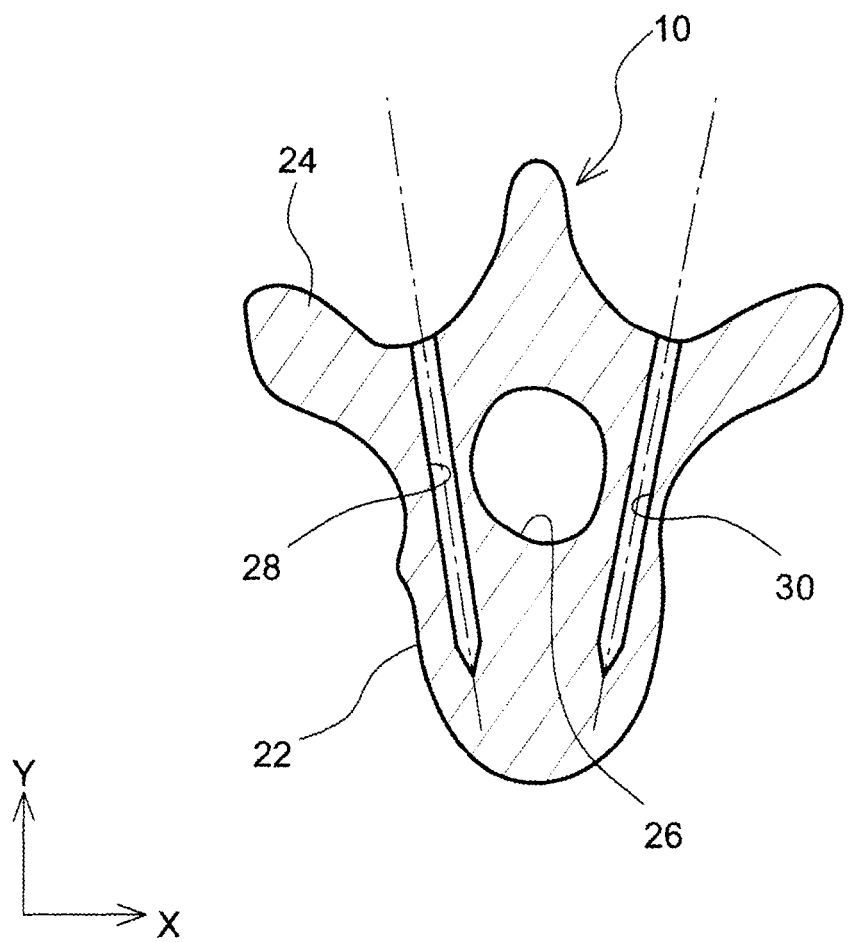
FIG. 2 is a diagram for explaining two guide holes formed in a vertebral bone.
Figure 3:
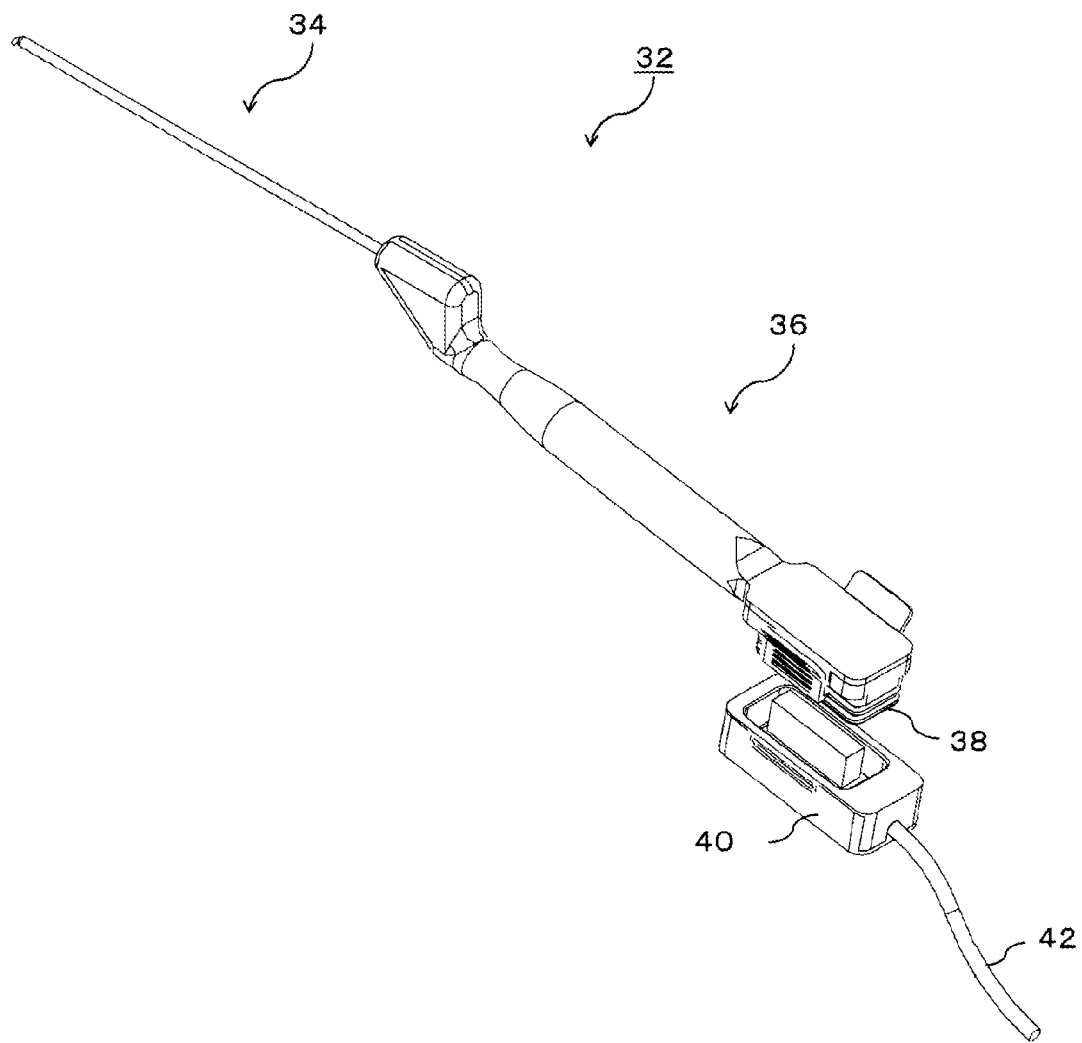
FIG. 3 is a perspective view of an ultrasonic probe for supporting spine surgery according to a preferred embodiment of the present invention.

FIG. 3 shows a preferred embodiment of an ultrasonic probe according to the present invention, and is a perspective view of the ultrasonic probe. A tissue insertion type ultrasonic probe according to the present embodiment specifically is an ultrasonic probe 32 for supporting spine surgery. The ultrasonic probe 32 is used when spine fixing surgery is performed using a metal tool. However, the technical characteristics described below can be applied to other tissue insertion type ultrasonic probes.

In FIG. 3, the ultrasonic probe 32 for supporting spine surgery comprises an insertion unit 34 and an operation unit 36. The insertion unit 34 is a shaft-shape member which extends along a central axis direction of the insertion unit 34. A rear end portion of the insertion unit 34 is connected to the operation unit 36. The operation unit 36 is a portion held by a user. A receptacle 38 is provided on a rear end of the operation unit 36. The receptacle 38 forms a connector, and a connector 40 to which a cable 42 is connected is detachably attached on the receptacle 38. Alternatively, the cable 42 may be directly connected to the operation unit 36.

Figure 4:
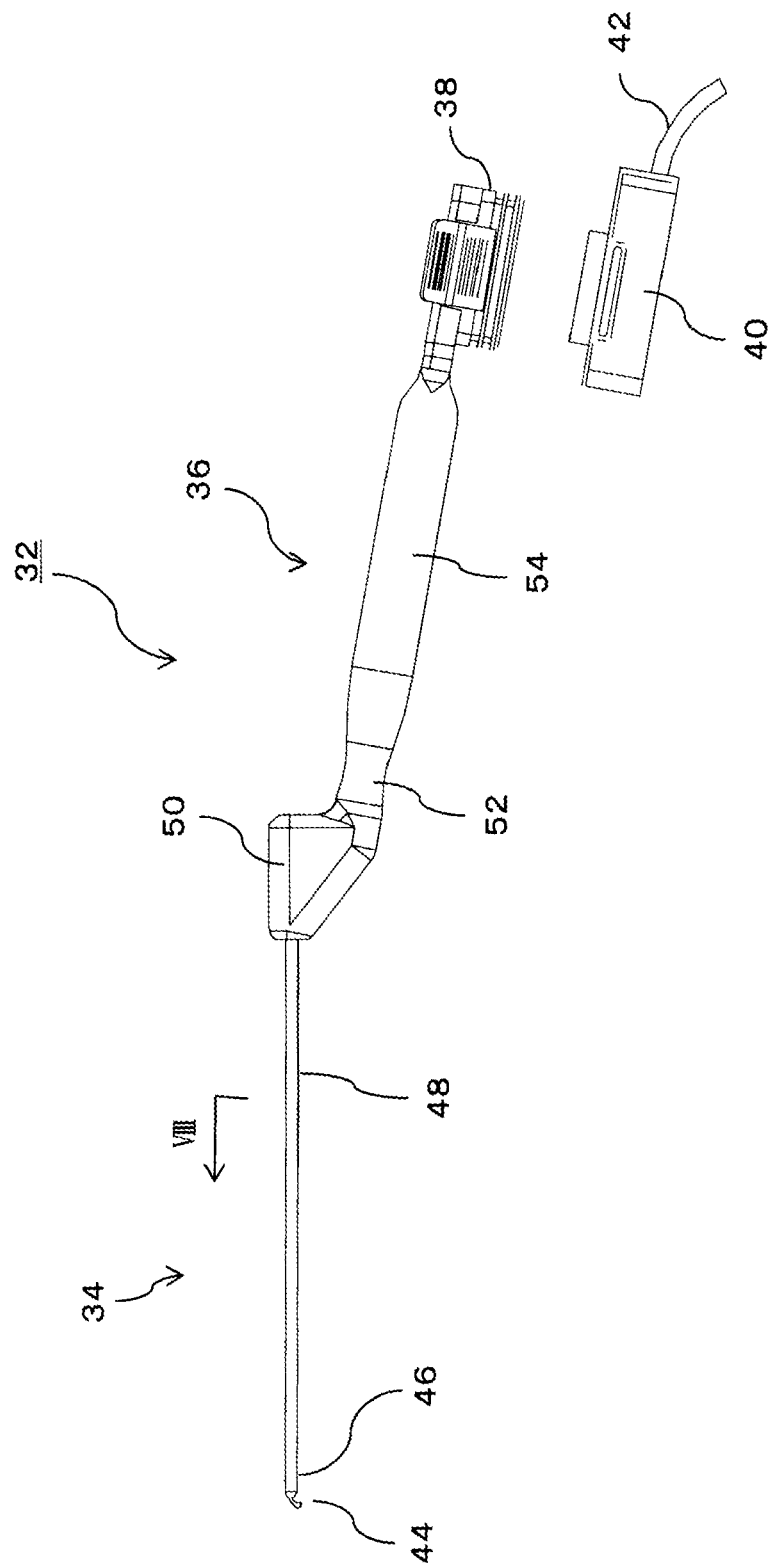
FIG. 4 is a side view of the ultrasonic probe for supporting spine surgery shown in FIG. 3.

FIG. 4 shows a side view of the ultrasonic probe 32 for supporting spine surgery shown in FIG. 3. The insertion unit 34 has a shape extending along a central axis direction of the insertion unit 34, and the insertion unit 34 is inserted into a guide hole formed in the vertebral bone. A tactile member (tactile tip) 44 is provided at a front end portion of the insertion unit 34. The tactile member 44 is contacted to an inner wall surface of the guide hole, and a vibration and a force caused by such contact are transmitted through an insertion shaft 48 and the operation unit 36 to a hand of the user. In addition to the tactile member 44, an array transducer 46 is provided at the front end portion of the insertion unit 34. The array transducer 46 comprises a plurality of transducer elements; an ultrasound beam is formed by the array transducer 46, and the ultrasound beam is electrically scanned. As will be described later, a transducer unit comprising the array transducer 46 is placed on the insertion unit 34.

The operation unit 36 is a portion held by the user, and comprises a connection portion 50, a neck portion 52, and a grip 54. In addition, as described above, the operation unit 36 comprises the receptacle 38 or the like. The connection portion 50 is a portion holding a rear end portion of the insertion unit 34, and, as shown in the figures, the connection portion 50 has a slightly enlarged shape. The neck portion 52 connected to the connection portion 50 is a narrowed portion which is slightly narrower than the grip 54. The grip 54 has a rod-like shape, and this portion is gripped and held by the user.

As shown in FIG. 4, the central axis of the insertion unit 34 and the central axis of the operation unit 36 intersect each other with a predetermined angle therebetween, so that the field of view in the front side is secured even in the state where the operation unit 36 is held. In the present embodiment, a magnetic sensor is provided on the connector 40, and a magnet is provided in the receptacle 38. In the state where the connector 40 is attached on the receptacle 38, a magnetic field of the magnet is detected by the magnetic sensor, and the attached state is electrically judged. The apparatus is desirably constructed so that a transmission signal is supplied only in such an attached state and the supply of the transmission signal is stopped in a state where the attached state is completed (is no longer maintained). With the use of the connector connection, it is possible to discard a portion that is nearer to the living body than is the connector 40; that is, a handpiece portion, after the use of the ultrasonic probe 32. In other words, the ultrasonic probe 32 itself can be used as a disposable member. In FIG. 4, reference numeral VIII shows a position of a cross section shown in FIG. 8.

Figure 5:
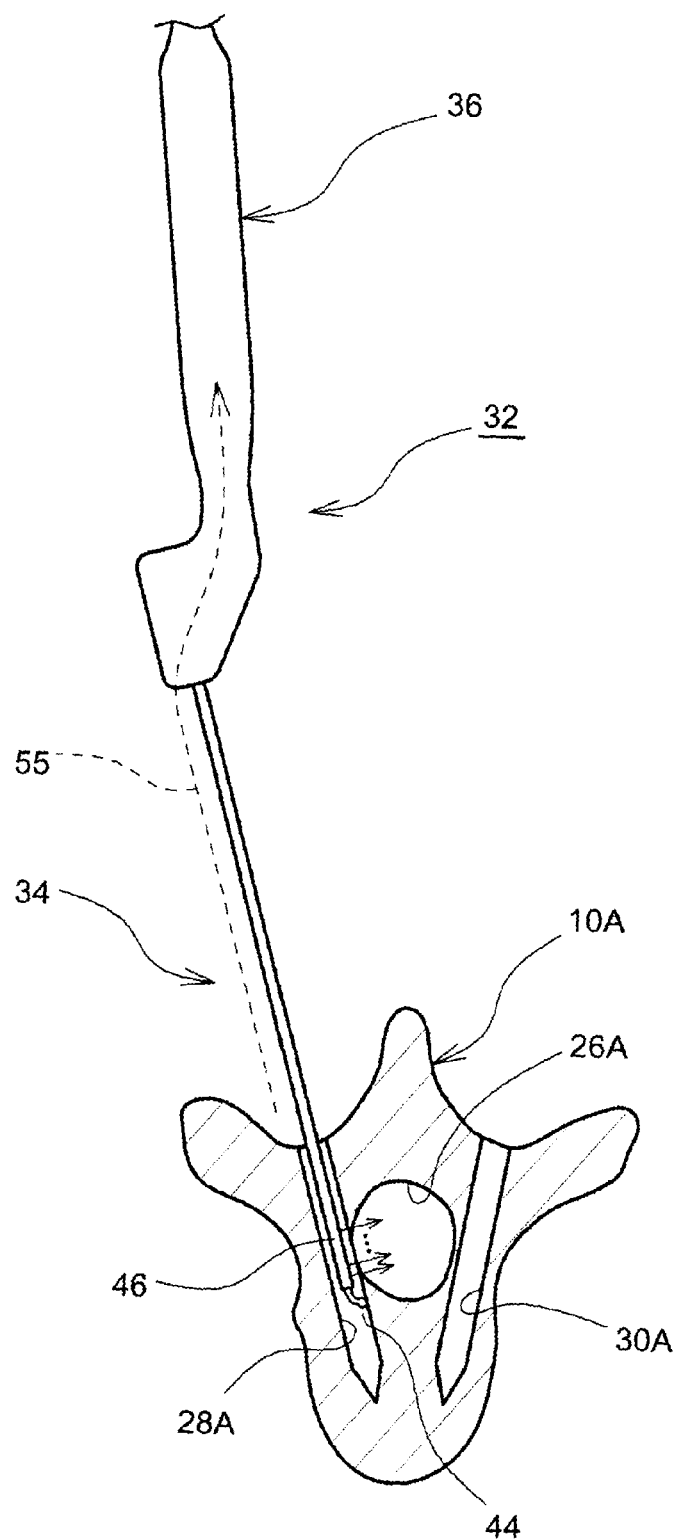
FIG. 5 is a diagram showing a usage state of the ultrasonic probe for supporting spine surgery shown in FIG. 3.

FIG. 5 shows an example use of the ultrasonic probe 32. As shown in FIG. 5, guide holes 28A and 30A are formed in a vertebral body 10A. These guide holes 28A and 30A are formed by means of a dedicated tool. In the formation process of the guide holes 28A and 30A, the ultrasonic probe 32 is used as necessary, to inspect the state of the insides of the guide holes 28A and 30A. With the ultrasonic probe 32 of the present embodiment, the shape of the inner wall of the guide hole can be inspected using the tactile sense. More specifically, the vibration transmitted from the tactile member 44 transmits through a path shown with reference numeral 55 to the operation unit 36, and the vibration is transmitted to the hand which holds the operation unit 36. By moving the tactile member 44 in the front or rear direction or rotating the tactile member 44, it is possible to understand the shape of the inner wall surface with the tactile sense. After this process or before this process, transmission and reception of ultrasound may be executed inside the guide holes 28A and 30A using the array transducer 36; that is, an ultrasound diagnosis may be executed. For example, the insertion unit 34 may be moved more deeply after the inner shape is inspected by the tactile sense using the tactile member 44, and then, the inside state of the vertebral body 10A may be inspected with the ultrasound diagnosis at a contact position of the tactile member 44.

For example, in FIG. 5, the guide hole 28A and a vertebral foramen 26A are very close to each other. Even if this state cannot be noticed by contact with the tactile member 44, with the ultrasound diagnosis, an image of the cross section in front of the array transducer 46 can be formed, and, thus, this state can be noticed on the screen at a deeper side from the surface of the guide hole 28A. Normally, an operation to enlarge stepwise the depth of the guide hole is executed, and the inside of the guide hole is inspected using the ultrasonic probe 32 at each stage. In the above description, the inspection by the ultrasound diagnosis is executed after the inspection by the tactile sense, but alternatively, these inspections can be executed simultaneously. In displaying the ultrasonic image, an image obtained by rotating a normal B mode image by 90° may be displayed.

Because the guide holes 28A and 30A are filled with liquid such as body fluid and cleaning fluid, no air layer would be interposed in the propagation path of the ultrasound, and a superior ultrasound propagation state can be realized. Therefore, it not necessary to closely contact all surfaces of the array transducer 46 or surfaces corresponding to the acoustic opening to the inner wall surface in the guide hole 28A. In other words, even if the front end portion of the tactile member 44 protrudes on the side of the living body in relation to the surface level of the insertion unit 34, no problem arises in the ultrasound diagnosis.

Figure 6:
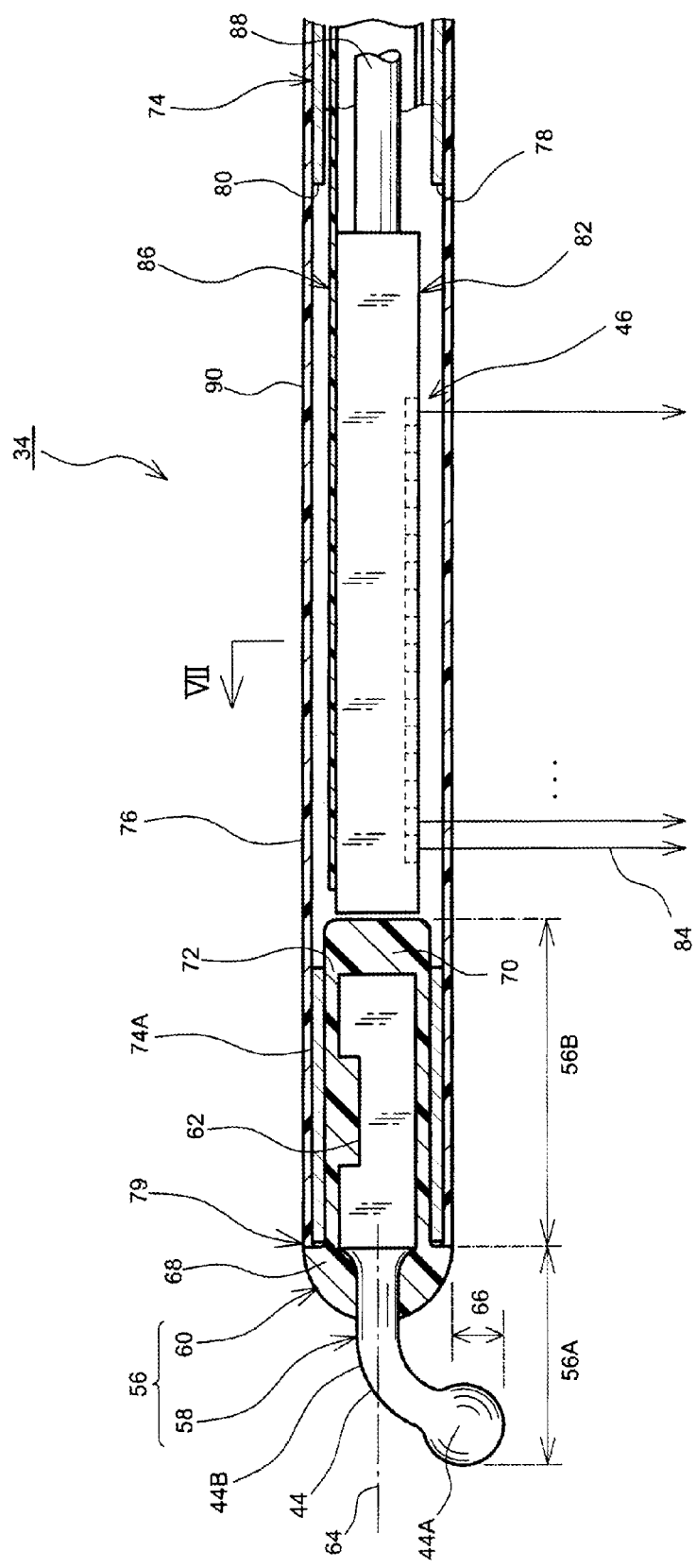
FIG. 6 is a cross-sectional diagram showing a structure of a front end portion of the ultrasonic probe for supporting spine surgery shown in FIG. 3.

FIG. 6 shows a structure of the front end portion of the insertion unit 34 as a cross-sectional view. A front-end component 56 is attached on the front end portion. The front-end component 56 is primarily formed with a metal component 58 and a resin component 60. The metal component 58 comprises the tactile member 44, and an anchor 62 connected to the tactile member 44. The tactile member 44 and the anchor 62 are integrated. That is, the tactile member 44 and the anchor 62 are formed as a single metal component. A material of the metal component 58 is, for example, stainless steel.

The resin component 60 comprises a cap portion 68, and a surrounding portion 70 connected to the cap portion 68. The cap portion 68 and the surrounding portion 70 are integrally molded, and are made of a material such as, for example, polyethylene. The resin component 60 may be formed by resin molding.

The front-end component 56 will now be described in more detail. The tactile member 44 comprises a head 44A and a shaft 44B. The head 44A has the shape of a small sphere, and has a diameter of, for example, 1.5 mm. The shaft 44B has a diameter of, for example, 0.8 mm. All or a part of the head 44A protrudes in the living body side in relation to a side surface level of the insertion unit 34 in a direction perpendicular to a central axis 64, with an amount of protrusion 66 of, for example, 1.0 mm. The shaft 44B extends along the central axis 64 of the front-end opening of the insertion unit 34 toward the front side, and is curved in the perpendicular direction described above. More specifically, the shaft 44B is curved toward a predetermined direction. The ultrasound diagnosis is executed toward this direction, as will be described below.

The anchor 62 has a cylindrical shape as a whole, but a part of the anchor 62 is cut out, so that a projection/depression structure exists on the side surface. This is a structural scheme to prevent the anchor 62 from being easily detached. The cap portion 68 has a dome-like shape protruding in the front side, and the shaft 44B described above protrudes in the front side from a center portion of the cap portion 68. The above-described surrounding portion 70 is connected on the back surface side of the cap portion 68, and has a cylindrical shape. The surrounding portion 70 surrounds the entirety of the anchor 62 having an overall cylindrical shape, and the outer diameter of the surrounding portion 70 matches the inner diameter of a pipe 74 serving as the tube member, as will be described below. In other words, the surrounding portion 70 is inserted in a front end portion 74A of the pipe 74. In this state, the side surface of the anchor 62 and the inner surface of the front end portion 74A of the pipe 74 are separated by a certain distance, and an intermediate portion 72 made of a resin member is present in the gap. The intermediate portion 72 forms a part of the surrounding portion 70. With the intermediate portion 72, insulation between the metal component 58 and the metal pipe 74 is maintained. Because the side surface of the anchor 62 is close to the inner surface of the front end portion 74A of the pipe 74, the vibration transmitted from the head 44A is effectively transmitted to the pipe 74 through the intermediate portion 72. In other words, the metal component 58 and the pipe 74 can be firmly connected mechanically or physically while the resin layer is interposed therebetween.

The outer diameter of the cap portion 68 in the example configuration of FIG. 6 matches an outer diameter of an insulating sheath tube 76. Alternatively, the outer diameter of the cap portion 68 may be matched with an inner diameter of the sheath tube 76 or an inner diameter of the pipe 74. In any case, in the present embodiment, a back side of the cap portion 68 and a front end of the insulating sheath tube 76 are adhered through thermal welding, and the cap portion 68 and the insulating sheath tube 76 are integrated. The integrated structure is shown in FIG. 6 as a thermal welding portion 79. With such a process, the front-end component 56 is connected to the sheath tube 76, and an outer assembly is formed by the front-end component 56 and the sheath tube 76. An inner assembly to be described later is inserted in the inside of the outer assembly.

The front-end component 56 may alternatively be considered as having an insertion portion 56B pressed into the inside of the pipe 74 and a portion in front of the insertion portion 56B; that is, a portion 56A protruding toward the front side in relation to the front end opening of the pipe 74. The portion 56A has, for example, a length of 4.0 mm, and the insertion portion 56B has, for example, a length of 6.0 mm. The outer diameter of the pipe 74 is, for example, 2.4 mm, and the inner diameter of the pipe 74 is, for example, 1.99 mm. The pipe 74 is made of a metal member in the present embodiment, and the metal member is, for example, stainless steel. The outer diameter of the insertion unit 34 is set in a range, for example, of 2.5 mm~3.0 mm, and the outer diameter of the insertion unit 34 in the present embodiment is, for example, 2.8 mm. A diameter of the anchor 62 is, for example, 1.4 mm, and a thickness of the intermediate portion 72 is, for example, 0.3 mm. The anchor 62 has a length of, for example, 5.0 mm. Therefore, an insulating layer of 1.0 mm is provided between the anchor 62 and a transducer unit 82 to be described later. The numerical values described in this specification are all merely exemplary values.

The structure of the insertion unit 34 will now be described in more detail. The insertion unit 34 comprises the above-described pipe 74. The pipe 74 is a tube member, and has a shielding function and a vibration transmitting function. In addition, the sheath tube 76 made of an insulating material is provided on an outside of the pipe 74. As the insulating material, for example, polyethylene or the like is known. The sheath tube 76 is made of a transparent material in the present embodiment, but may alternatively be made of a colored material. Two openings 78 and 80 are formed at the front end portion of the pipe 74. Of the two openings 78 and 80, the opening 78 functions as an opening for the ultrasound. The opening 80 is formed in order to improve workability during manufacturing. The transducer unit 82 is provided in a deeper side of the opening 78; that is, inside the pipe 74. The transducer unit 82 comprises the array transducer 46. The array transducer 46 comprises a plurality of transducer elements arranged in the axial direction. An ultrasound beam 84 is formed by the array transducer 46, and is electrically scanned. With this process, a scanning surface which is a two-dimensional data reading region is formed. Echo data obtained on the scanning surface is two-dimensionally mapped so that a two-dimensional tomographic image (B mode image) can be formed. In the present embodiment, a plurality of ultrasound beams 84 are formed, and all ultrasonic beams pass through the opening 78. In other words, the opening 78 is formed in a size so as not to block propagation of the ultrasound during transmission and reception.

An FPC (flexible printed circuit) board 86 is attached to the transducer unit 82. The FPC board 86 is a sheet member or a film member for lines. For example, a large number of signal lines are formed by printing on an insulating base sheet. In the present embodiment, the array transducer 46 comprises 50 transducer elements, and, therefore, at least 50 signal lines are formed on the FPC board 86. The signal lines form a signal line array. The FPC board 86 is a board attached to the transducer unit 82, and the FPC board 86 is connected to another FPC board (not shown in FIG. 6). A thin foil made of copper is provided on the living body side of the array transducer 46, and functions as a ground electrode. A conductor of a cable 88 serving as a ground line is connected to the ground electrode. The cable 88 extends to the rear end side using the space of the center portion of the pipe 74. The other FPC board described above is rounded and inserted along the inner wall surface of the pipe 74. These structures will be described later in more detail. One or a plurality of matching layers are provided on the living body side of the array transducer 46 as necessary, and an acoustic lens is also provided as necessary. In the present embodiment, a molding member 90 fills the surrounding of the transducer unit 82, and the molding member 90 is an adhesive. The molding member 90 is formed with a material having an acoustic impedance close to that of the living body, in order to not block propagation of the ultrasound. The material of the sheath tube 76 also is preferably a material having an acoustic impedance close to the acoustic impedance of the living body.

The array transducer 46 is aligned in a direction matching a direction in which the tactile member 44 extends. That is, the ultrasound beam is formed in the insertion unit 34 in a direction where inspection by tactile sense is desired. Alternatively, these directions may be separately determined. With the matching of the directions as in the present embodiment, however, it becomes possible to execute the ultrasound inspection after the tactile inspection by contact, at the same site without axially rotating the ultrasonic probe. Alternatively, the ultrasound beam may be formed in a direction in front and to the side of the transducer unit 82 using a deflection scan technique. In the present embodiment, an electrical linear scan method is used, but alternatively, other electronic scan methods such as an electronic sector scanning method may be applied. Alternatively, a 2D array transducer may be provided.

Figure 7:
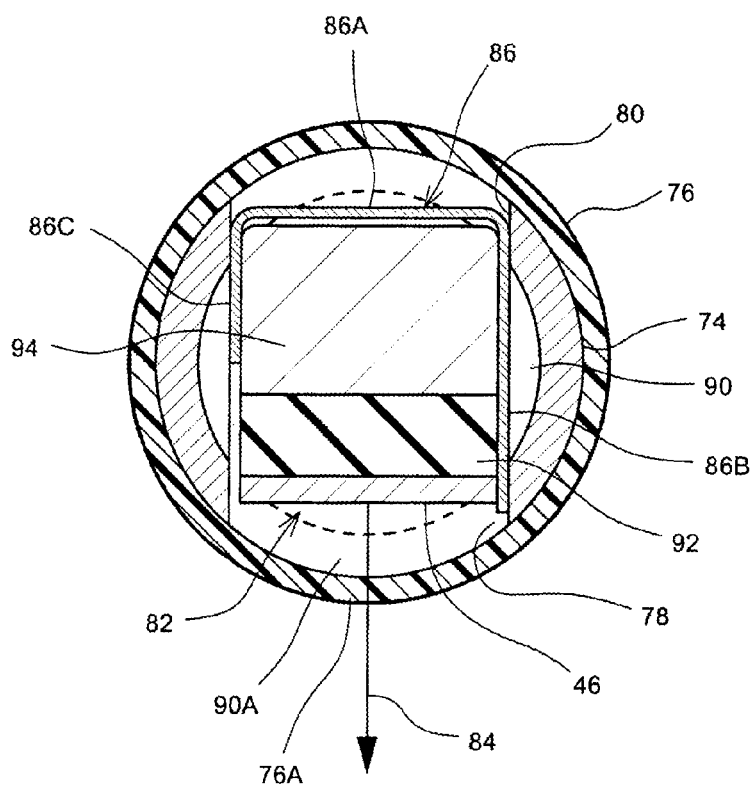
FIG. 7 is a cross-sectional diagram of a transducer unit shown in FIG. 6.

FIG. 7 shows a cross sectional view of a position shown in FIG. 6 with reference numeral VII. In FIG. 7, the pipe 74 is provided inside the sheath tube 76. From a different point of view, the sheath tube 76 is provided to cover the pipe 74. The two openings 78 and 80 are formed in the pipe 74, and, in FIG. 7, the opening 78 is shown at the lower side and the opening 80 is shown at the upper side. The transducer unit 82 is provided in the pipe 74. As described above, the transducer unit 82 comprises the array transducer 46, and a backing 92 on the back surface side. A pedestal 94 is provided on the back surface side. On the living body side of the array transducer 46; that is, in the front side of the array transducer 46, one or a plurality of matching layers are provided as necessary. The molding member 90 is provided around the transducer unit 82. In particular, a molding member 90A is provided on the front side of the array transducer 46, so that ultrasound propagation is secured. The ultrasound passes through the molding member 90A and a part 76A of the sheath tube. The FPC board 86 is provided surrounding the transducer unit 82. The FPC board 86 comprises three portions 86A, 86B, and 86C, which are provided on three respective surfaces. The copper foil described above with reference to FIG. 6 is not shown in FIG. 7. A thickness of the molding member shown with reference numeral 90A is, for example, 0.3 mm. A plurality of signal lines which are connected to the plurality of transducer elements are formed on the FPC board 86 by printing. A rear end portion of the FPC board 86 is connected to the front end portion of the other FPC board through thermo compression bonding. With this configuration, the signal line array of one board and the signal line array of the other board are electrically connected to each other in a one-to-one relationship. Alternatively, a ground line may be provided on the FPC board 86, or the ground line may be extended by means of a cable as described above.

Figure 8:
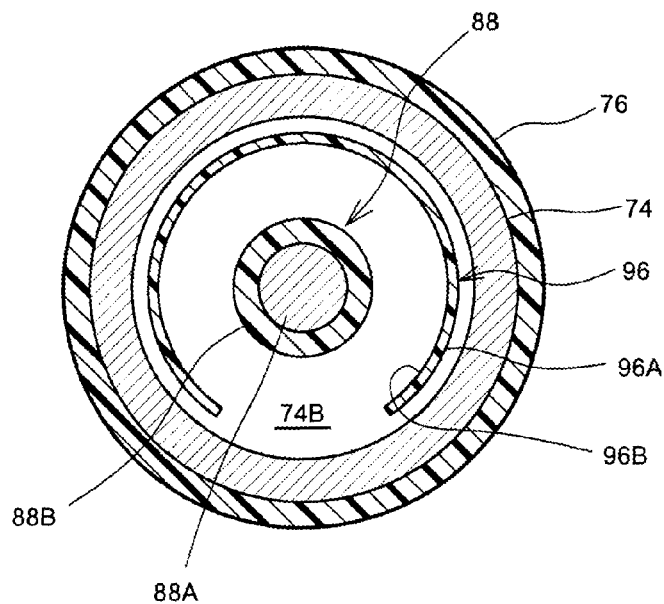
FIG. 8 is a cross-sectional diagram of an insertion shaft shown in FIG. 4.

FIG. 8 shows a cross section at an intermediate position of the insertion unit. As described above, the sheath tube 76 is provided on the outside of the pipe 74. As shown in FIG. 8, an FPC board 96 is provided in an inside space 74B of the pipe 74. The FPC board 96 is a long-and-narrow sheet having a band shape extending from a front end portion to the rear end portion of the insertion unit, and is curved in the pipe 74 along the inner surface of the pipe 74. That is, as shown in FIG. 8, the FPC board 96 is inserted in the pipe 74 in a rounded shape like a tube. The concept of the "tube" includes a semi-cylindrical shape or the like. The FPC board 96 may have the C-shape before insertion into the pipe 74 or may be curved according to the shape of the inner wall surface of the pipe 74 to become the C-shape as shown in FIG. 8. The concept of the "C-shape" includes an arch shape.

A large number of signal lines are formed on the FPC board 96 by printing, along the width direction; that is, the curving direction, and form a signal line array. Each signal line is a line extending in the axial direction. With the use of the printing technique, each line can be formed with a very narrow width, and the pitch between adjacent lines can be set to a very low value. Therefore, a large number of signal lines can be easily formed at a high density over the FPC board 96. One or a plurality of ground lines may be formed over the FPC board 96 as necessary, or a signal line array may be formed on one surface side, and the other surface side may be set as a solid electrode for grounding. In the present embodiment, the FPC board 96 is curved in the pipe 74 in the C-shape as described above. That is, one end edge and the other end edge are distanced from each other. The FPC board 96 substantially has a shape close to a cylinder, but the ends are distanced from each other with a certain gap region. With such a structure, because no overlap of the ends occurs, there can be obtained an advantage that cross-talk can be prevented or reduced. Alternatively, a shield line or a ground line may be appropriately provided and an overlap of the ends may be caused. The FPC board may be inserted with a whirl-like shape or the FPC board may be inserted in a spiral-like shape. As an alternative configuration, a folded shape may be considered.

As shown in FIG. 8, a certain partial space is created inside the FPC board 96 having a rounded shape along the central axis, and, from the viewpoint of using such a dead space, the cable 88 is provided in the partial space in the present embodiment. The cable 88 comprises a central conductor 88A and a cover 88B. With such a configuration, the ground can be formed using also a wide conductor, and, therefore, there can be obtained an advantage that a superior ground can be constructed. In the present embodiment, one cable is inserted into the pipe 74. However, if more space is available, a plurality of cables may be inserted. When a large number of cables are inserted, the vibration transmission function of the pipe 74 may be obstructed, and, therefore, the inner structure is desirably determined so that such a disadvantage does not arise. Thus, when space is available, a plurality of FPC boards may be inserted in a curved state into the pipe 74. With the normal curved shape as shown in FIG. 8, there can be obtained an advantage that the FPC board 96 may be easily inserted into the pipe 74. For example, it is very difficult to insert 50 wires or cables into a very narrow pipe, but in the present embodiment, there can be obtained an advantage that such a large number of signal lines can be easily placed. The FPC board 96 has an elastic function, and a restoration force from the curved shape to the flat shape is always present. Therefore, the FPC board 96 naturally contacts the inner surface of the pipe 74. With this structure, it is possible to minimize the radius of curvature of the FPC board 96 and to minimize the distortion caused in the FPC board 96.

In the curved shape shown in FIG. 8, the signal line array may be formed on one of an outer side surface 96A of the FPC board 96 and an inner side surface 96B of the FPC board 96. Alternatively, the signal line array may be formed on both surfaces 96A and 96B. The pipe 74 is formed with a conductor and is grounded. Therefore, there can be obtained an advantage that noise from outside can be blocked with the pipe 74.

Figure 9:
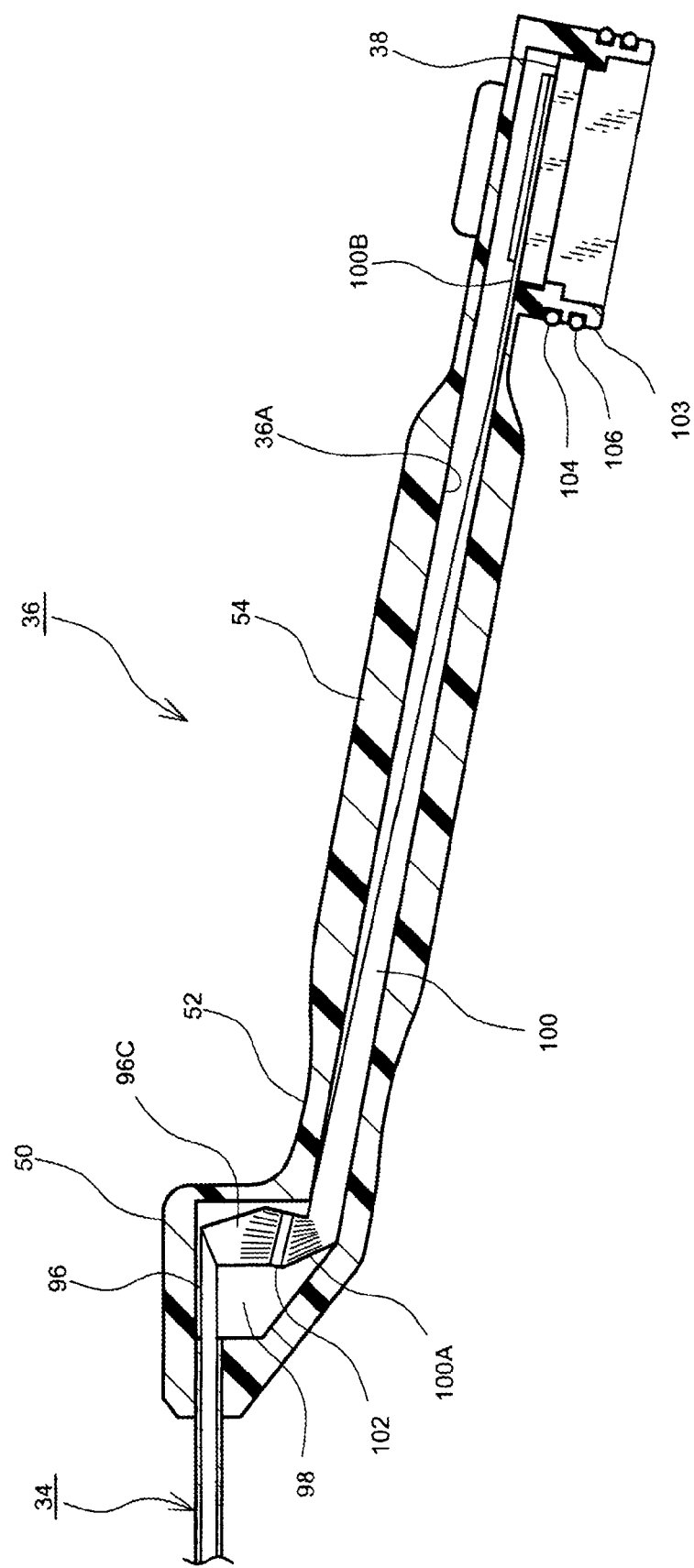
FIG. 9 is a cross-sectional diagram of an operation unit.

FIG. 9 shows a cross sectional diagram of the operation unit 36. As described above, the operation unit 36 comprises the grip 54 and the neck portion 52, and further comprises a connection portion 50. An FPC board 100 is provided in an inside space 36A of the operation unit 36. The FPC board 100 has a shape of a band extending in the axial direction of the operation unit 36, and the front end portion 100A of the FPC board 100 is enlarged in the width direction. In the connection portion 50, a slightly enlarged space 98 is formed, and the rear end portion of the FPC board 96 passing through the pipe as described above extends into the space 98. Specifically, the rear end portion 96C exiting the pipe is enlarged in the width direction, and is connected to the front end portion 100A of the FPC board 100 described above. More specifically, the signal line array of one side and the signal line array of the other side are electrically and physically connected to each other in a one-to-one relationship by thermo-compression bonding. The thermo-compression bonded portion is shown by a reference numeral 102. By adhering after the end portions are enlarged, it is possible to increase an allowance range of the position deviation in the width direction, and the cross-talk between signal lines can be effectively prevented. Therefore, there can be obtained an advantage that the workability can be improved. The shape of the signal line array can be easily designed using the printing technique.

As shown in FIG. 9, the FPC board 100 passes through the inside of the operation unit 36, and the rear end portion of the FPC board 100 is electrically connected to the receptacle 38.

In this case also, the thermo-compression bonding is employed. With this structure, the electrical connection with the connector on the side of the cable is achieved through the receptacle 38. Reference numerals 104 and 106 represent O-rings. Reference numeral 103 represents a frame when the connector connection is realized. Alternatively, an adhering force may be generated using magnetic force. In FIG. 9, the cable which forms the ground line is not shown. The cable is connected from the inside of the connection portion 50 through the inside space 36A to a ground terminal of the receptacle 38. Alternatively, this connection may be realized using a relay cable. In the FPC boards 96 and 100, a plurality of signal lines are aligned in the lateral width direction, and, in the present embodiment, the signal line arrays are arranged on one surface. Alternatively, a multilayer board or the like may be employed to three-dimensionally arrange the plurality of signal lines.

Next, a method of manufacturing the ultrasonic probe will be described in detail with reference to FIGS. 10-18.

Figure 10:
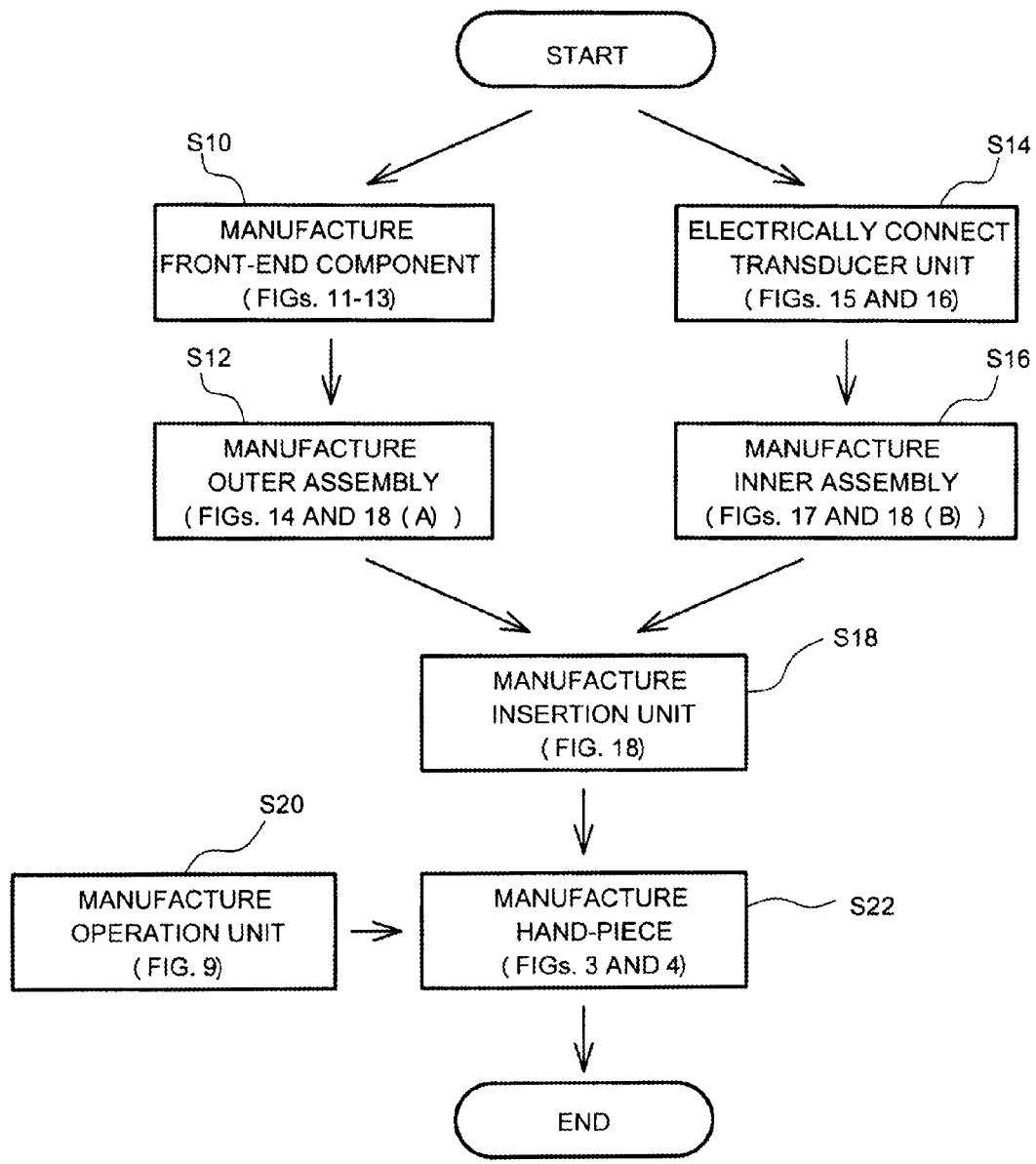
FIG. 10 is a flowchart showing a method of manufacturing an ultrasonic probe according to a preferred embodiment of the present invention.
Figure 11:
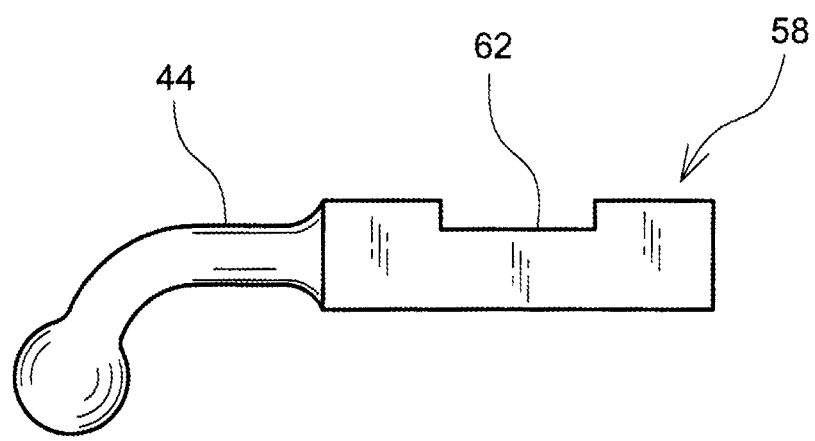
FIG. 11 is a side view of a metal component.
Figure 12:
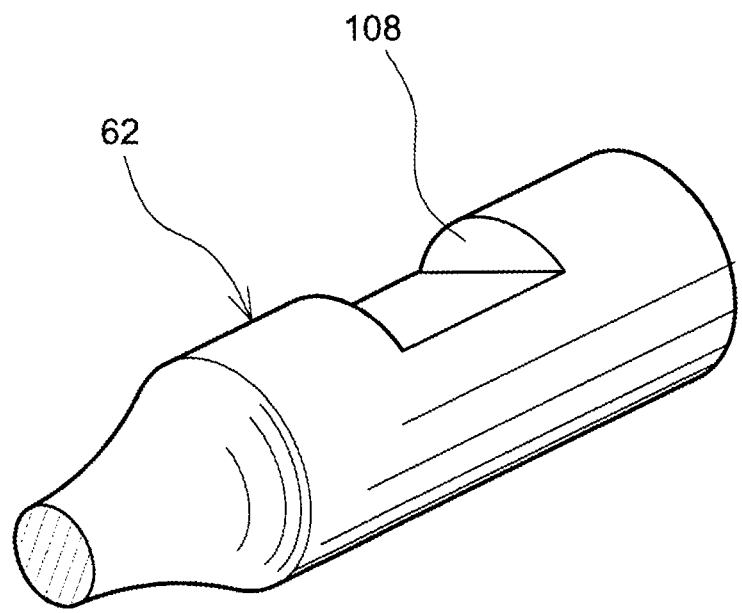
FIG. 12 is a perspective view of an anchor in a metal component.
Figure 13:
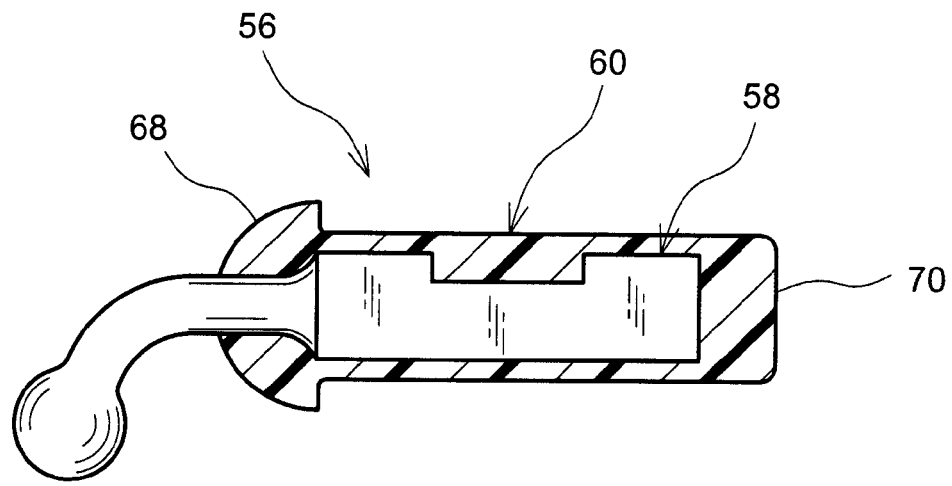
FIG. 13 is a cross-sectional diagram of a front-end component.

In S10 shown in FIG. 10, the front-end component is manufactured. This process will be described with reference to FIGS. 11-13. FIG. 11 shows the metal component 58, which comprises the tactile member 44 and the anchor 62. FIG. 12 shows a perspective view of the anchor 62. In the example configuration of FIG. 12, one recess 108 is formed on the side surface of the anchor 62, which is a structure for preventing detachment. Alternatively, a projection may be formed in place of the recess 108, or a plurality of recesses or the like may be formed. As shown in FIG. 13, the front-end component 56 is manufactured with a molding process on the metal component 58 to provide the molding member 60 surrounding the anchor 62. That is, the molding member 60 is the resin component as described above (FIG. 6), and comprises the cap portion 68 and the surrounding portion 70.

Figure 14:
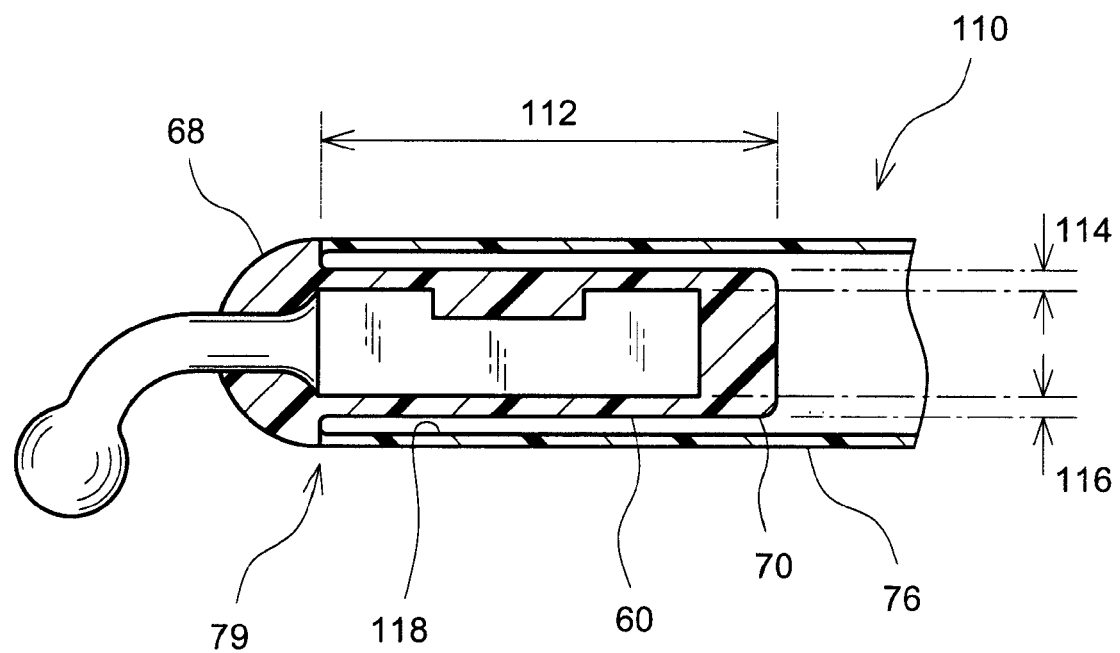
FIG. 14 is a cross-sectional diagram showing a front end portion of an outer assembly.

Referring back to FIG. 10, in S12, the outer assembly is manufactured. A structure of the outer assembly is shown in FIG. 14, and also in FIG. 18(A). In FIG. 14, in manufacturing the outer assembly 110, an operation to adhere the front edge of the sheath tube 76 to the back surface of the cap portion 68 of the resin component 60 by thermal welding is executed. Reference numeral 79 shows the thermal welding portion. In the example configuration of FIG. 14, the outer diameter of the cap portion 68 and the outer diameter of the sheath tube 76 match each other, but such matching of size is not necessary, so long as the thermal welding can be executed. In the front end portion of the sheath tube 76, the surrounding portion 70 is provided while being distanced from the inner surface of the sheath tube 76, and a slit 118 having a cylindrical shape is formed around the surrounding portion 70. As will be described later, the front end portion of the pipe is inserted into the slit 118. Thicknesses 114 and 116 are preferably set in a range such that insulation can be reliably secured and the mechanical connection can be firmly achieved. In the manufacturing of the outer assembly 110, the thermal welding operation as described above is executed, and the front end side of the sheath tube 76 is completely sealed.

Figure 15:
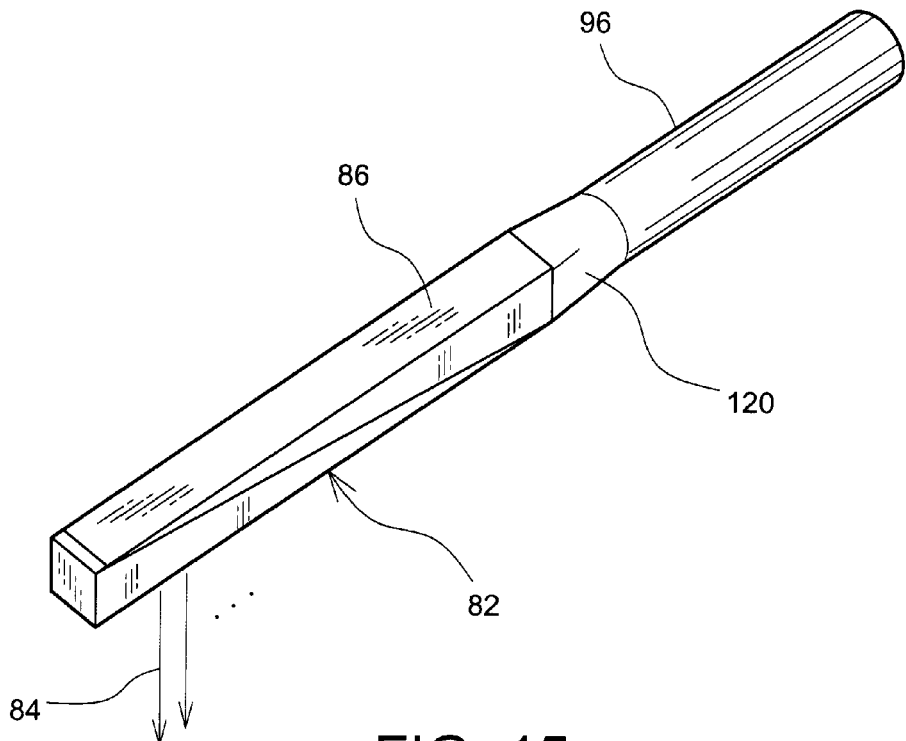
FIG. 15 is a first perspective view showing a transducer unit to which an FPC board is attached.
Figure 16:
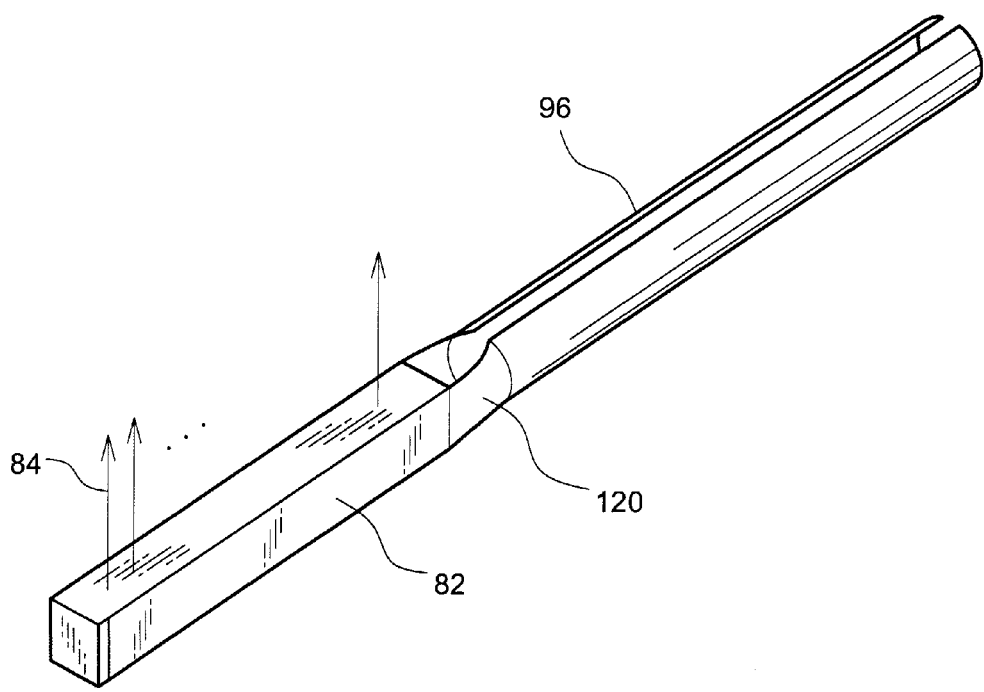
FIG. 16 is a second perspective view showing a transducer unit to which an FPC board is attached.

Referring back to FIG. 10, in S14, an operation of electrically connecting to the transducer unit is executed. This process will be described with reference to FIGS. 15 and 16. FIG. 15 is a diagram showing the transducer unit 82 viewed from above, and FIG. 16 is a diagram showing the transducer unit 82 viewed from below. In FIG. 15, the FPC board 86 is attached to the transducer unit 82, and the extending end of the FPC board 86 is connected to the front end portion of the FPC board 96. The connection portion is shown as a thermal compression bonding portion 120. The FPC board 96 is inserted and placed in the pipe, with a tube-like rounded shape. The signal line array on the FPC board 86 and the signal line array on the FPC board 96 are individually connected. In this manner, the signal lines are connected individually to the transmission/reception channels; that is, the transducer elements, in the transducer unit 82. In FIG. 16, the FPC board 96 in the rounded state is shown, and a cable for the ground is passed through this structure, but the cable is not shown in FIG. 16. Reference numeral 84 represents a direction of the ultrasound beam. The structure shown in FIGS. 15 and 16 is merely exemplary.

Figure 17:
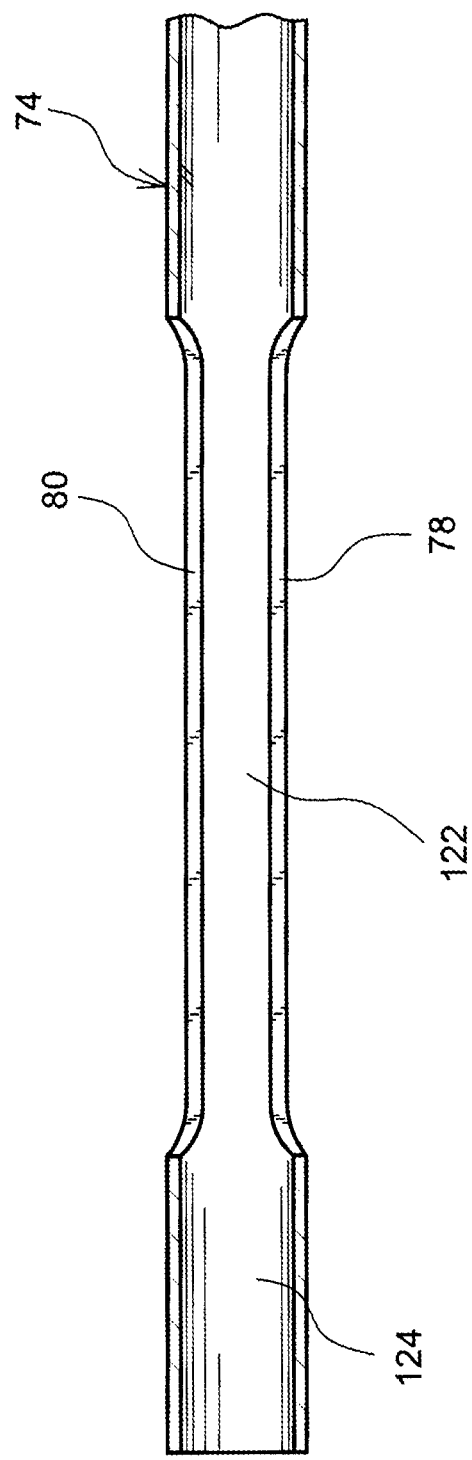
FIG. 17 is a cross-sectional diagram showing a front end portion of a pipe.

Referring back to FIG. 10, after the electrical components are manufactured as described above, in S16, the inner assembly is manufactured. This process will be described with reference to FIG. 17 and FIG. 18(B). FIG. 17 shows the front end portion of the pipe 74. The openings 78 and 80 are formed in the front end portion, and a space between the openings 78 and 80 is a placement space 122 for the transducer unit. On a front side, an insertion space 124 of the front-end component is present. As described above, the opening 80 on the upper side does not need to be formed. As shown in FIG. 18(B), the transducer unit is inserted into the pipe 74 through any of the openings. Before the insertion, the FPC board connected to the transducer unit 82 is inserted to the rear end side into the pipe 74 in a curved shape. As shown in FIG. 9, the rear end portion of the FPC board 96 is enlarged, and, therefore, the rear end portion is rounded into a smaller shape when the FPC board 96 is inserted into the pipe 74. Alternatively, after the transducer unit 82 is placed, the FPC board which is already attached to the transducer unit 82 and the FPC board which is already rounded and inserted into the pipe may be connected within the pipe. For the placement of the transducer unit 82, an adhesive or the like is used. Alternatively, the transducer unit may be inserted from the rear end side of the pipe 74.

Figure 18:
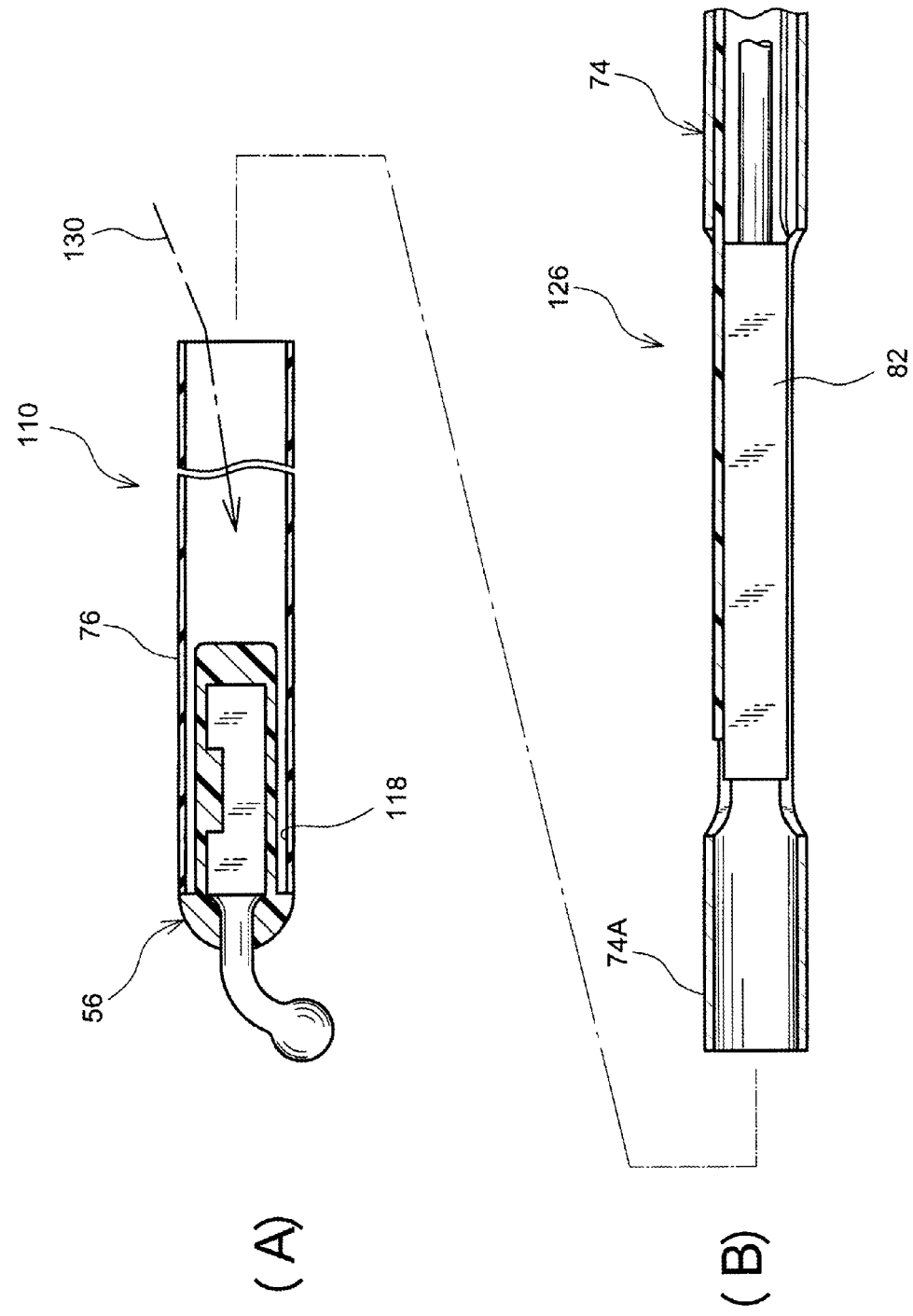
FIG. 18 is a diagram for explaining insertion of an inner assembly into an outer assembly.

Referring back to FIG. 10, in S18, the insertion unit is manufactured as shown in FIG. 18. Specifically, FIG. 18(A) shows the outer assembly 110, and FIG. 18(B) shows the inner assembly 126. The inner assembly 126 is inserted into the inside of the outer assembly 110 from the rear end side of the outer assembly 110. Prior to the insertion process, as shown by reference numeral 130 in FIG. 18, an adhesive is injected into the front end portion of the outer assembly 110. The adhesive forms the molding member around the transducer unit. With the insertion of the inner assembly 126 into the outer assembly 110, the insertion unit in the front-end component is inserted into the front end portion 74A of the pipe 74. That is, the front end portion of the pipe 74 is fitted to the slit having the cylindrical shape. As described above, the front-end component is already molded, and is welded and integrated with the sheath tube. Therefore, by merely inserting the inner assembly 126 into the outer assembly 110, an appropriate position relationship can be achieved between the front end portion 74A of the pipe 74 and the anchor, and, thus, to appropriately position these components.

Referring back to FIG. 10, in S22, the operation unit manufactured in S20 is connected to the insertion unit, and, with this process, a hand-piece is manufactured. The operation unit is shown in FIG. 9 described above, and the hand-piece is shown in FIGS. 3 and 4 described above.

Figure 19:
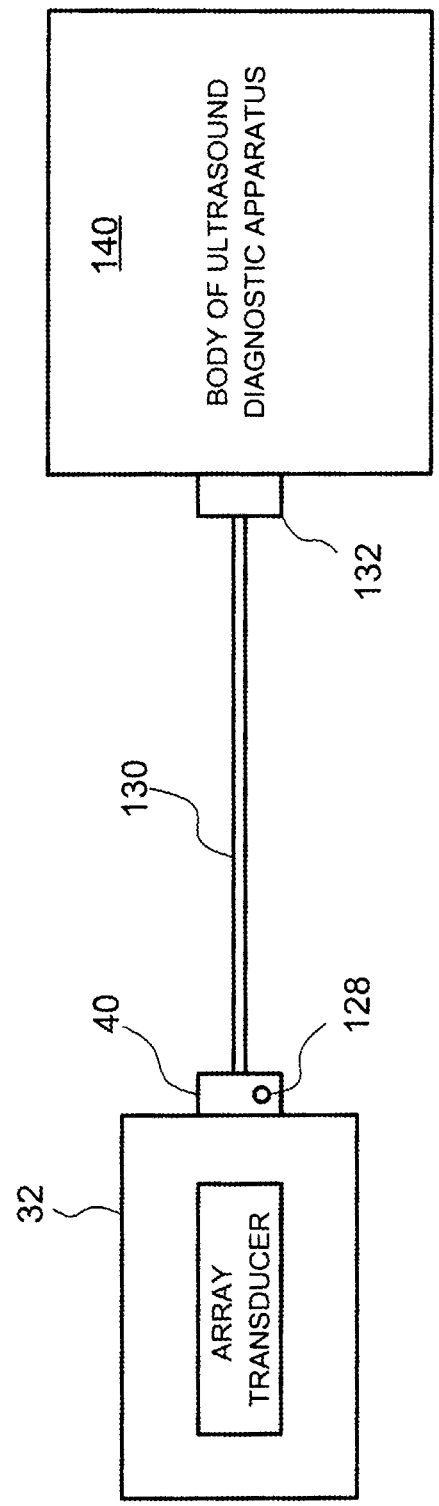
FIG. 19 is a diagram showing an example structure of an ultrasound diagnosis system.
Figure 20:
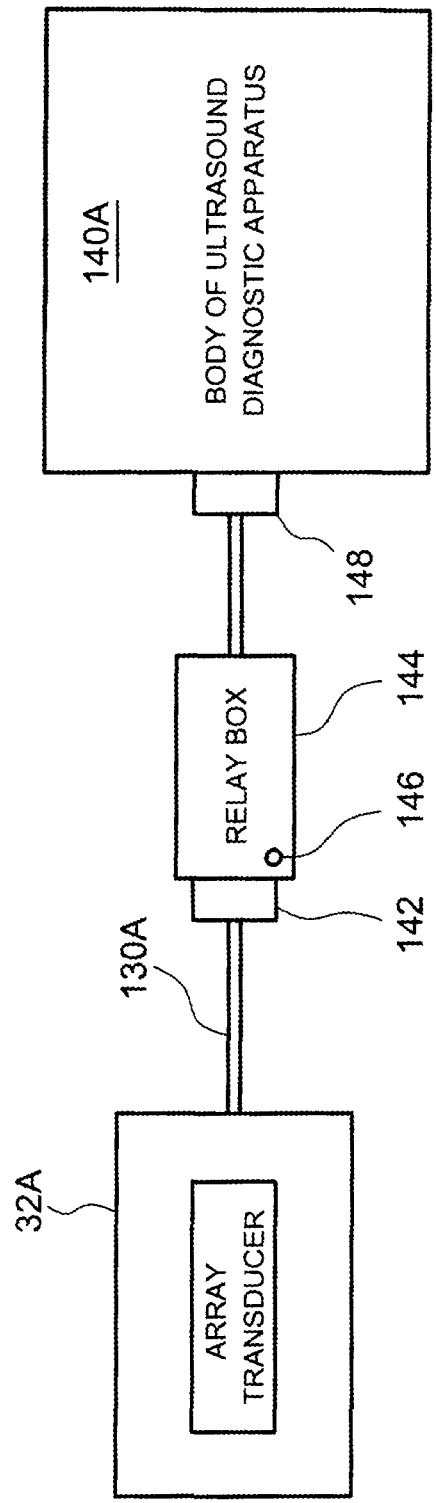
FIG. 20 is a diagram showing another example structure of an ultrasound diagnosis system.

FIGS. 19 and 20 show an example system configuration. In the example configuration shown in FIG. 19, the ultrasonic probe 32 for supporting spine surgery comprises an array transducer, and the connector 40 is detachably attached to the receptacle of the probe. The connector 40 comprises a magnetic sensor 128, and the connector attachment state is judged by detecting a magnetic field. The cable 130 is attached to the connector 40, and a connector 132 is provided on the other end side of the cable 130, which is detachably attached to a body 140 of an ultrasound diagnosis apparatus. In such a structure, when the ultrasonic probe 32 is to be discarded after use, the connector 40 may be removed.

FIG. 20 shows another example system configuration. An ultrasonic probe 32A comprises the array transducer. A cable 130A is connected to the ultrasonic probe 32A in a fixed manner, and a connector 142 is provided on an end of the cable 130A. The connector 142 is detachably attached to a relay box 144. The attachment may be detected using a magnetic sensor 146. A cable is attached to the relay box 144, and a connector 148 is provided on an end of the cable. The connector 148 is detachably attached to a body 140A of an ultrasound diagnostic apparatus. The body 140A of the ultrasound diagnostic apparatus comprises a transmission unit, a reception unit, an image formation unit, a display, an operation panel, etc.

According to the embodiment described above, a tissue insertion type ultrasonic probe which can execute both the tactile inspection and ultrasound diagnosis can be formed. In addition, according to the embodiment described above, even if the diameter of the insertion unit is reduced, a large number of signal lines can be simply and easily provided in the insertion unit. Moreover, according to the embodiment described above, in a state where an insertion portion in the front-end component is inserted into the pipe, the anchor and the pipe are firmly connected mechanically while being electrically insulated. Therefore, there can be obtained an advantage that superior transmission of vibration can be achieved while insulation is secured.

Figure 21:
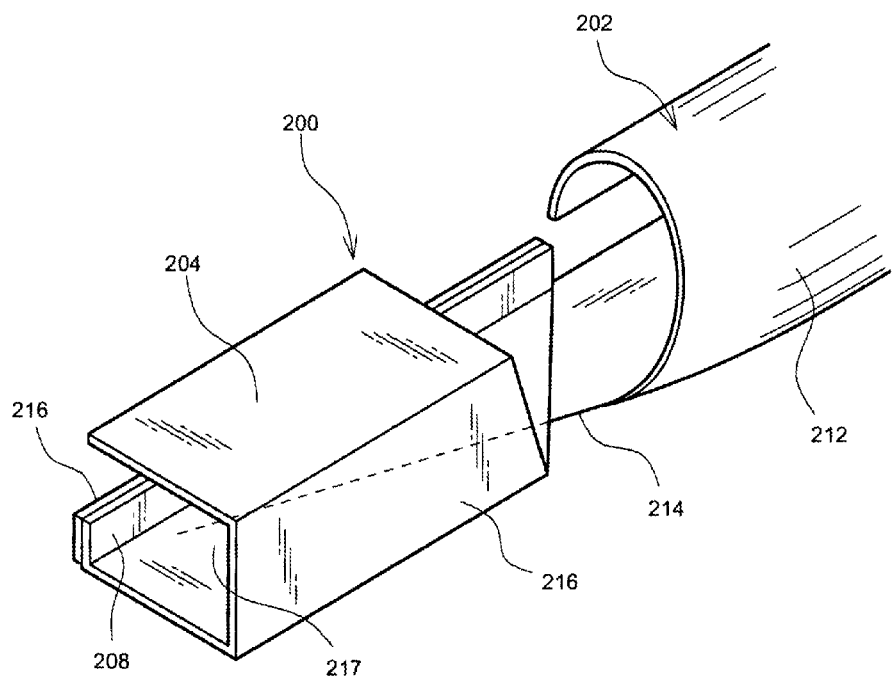
FIG. 21 is a perspective view showing a line assembly structure according to another preferred embodiment of the present invention.
Figure 22:
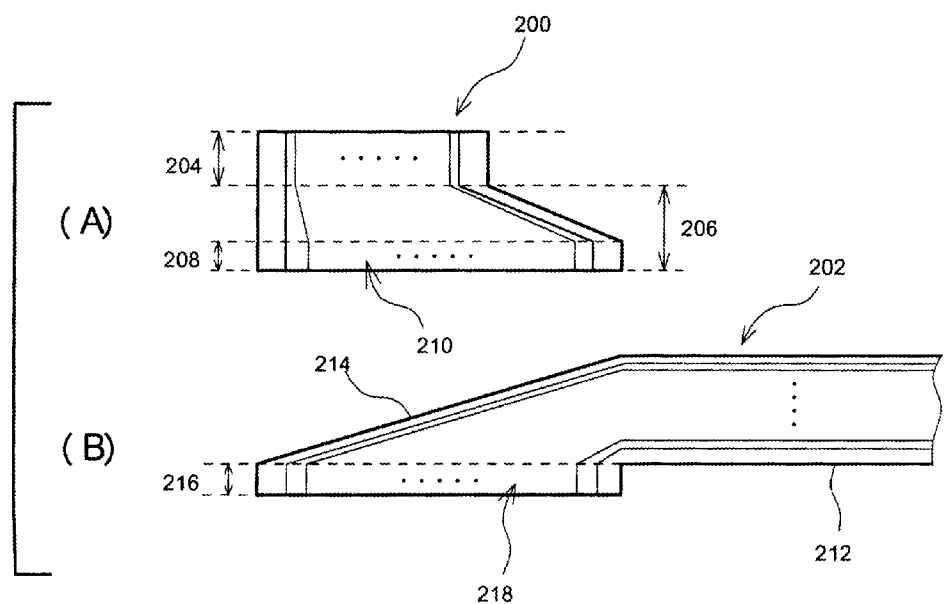
FIG. 22 is a diagram showing two FPC boards forming the line assembly structure shown in FIG. 21.

FIGS. 21 and 22 show a structure of primary portions of another embodiment of the present invention. A line assembly structure shown in FIG. 21 is constructed within a front end portion of the pipe forming a part of the insertion unit. Specifically, an FPC board 200 is attached to a transducer unit (not shown). An FPC board 202 is inserted in a rounded shape in the pipe. FIG. 22(A) and FIG. 22(B) show an expanded view of the FPC board 200 and the FPC board 202. The FPC board 200 comprises a portion 204 connected to the array transducer in the transducer unit and a portion 206 extending from the portion 204. The portion 206 is enlarged, and an end (extension end) 208 of the portion 206 forms a contact portion. The FPC board 200 comprises a signal line array 210. In the signal line array 210, an inter-line pitch in the contact portion 208 is larger than an inter-line pitch in the portion 204. The FPC board 202 comprises a body portion 212 and an enlarged end 214, and a front end portion of the end 214 forms a contact portion 216. The FPC board 202 comprises a signal line array 218. In the signal line array 218, an inter-line pitch in the contact portion 216 is larger than an inter-line pitch in the body portion 212. Inter-line pitches (line patterns) of two contact portions 208 and 216 are identical to each other, and the contact portions 208 and 216 are overlapped and connected through methods such as pressurization adhesion.

In FIG. 21, reference numeral 217 represents a space in which a backing or the like is placed in the transducer unit. The array transducer is provided on an upper side of the portion 204 of the FPC board 200. A copper foil which forms a ground electrode is provided on an upper side of the array transducer. The ground line is not shown in FIG. 21. In a state where the FPC board 200 is attached to the transducer unit, the FPC board 202 is connected to the combined structure. Then, the FPC board 200 is folded in a manner to enclose the backing of the transducer unit. With this process, the end 214 of the FPC board 202 is also folded. The body portion 212 of the FPC board 202 is set in a rounded state in the pipe.

When the above-described line assembly structure is placed in the pipe, first, in a state where the line assembly structure is connected to the transducer unit, a rear end portion of the rounded FPC board 202 is inserted into an opening formed on a front end portion of the pipe, and the rear end portion is gradually sent into the pipe. The rear end portion is then pulled out from a rear end opening of the pipe to the outside. Then, the transducer unit is fixed on a predetermined position of the front end portion of the pipe using an adhesive or the like. According to the structure shown in FIGS. 21 and 22, two FPC boards can be reliably and easily connected. Because the inter-line pitch is widened at the two contact portions, the workability during connection is superior. In addition, a problem of erroneous line connection tends not to occur.

What is claimed is:

1. An ultrasonic probe for supporting spine surgery, comprising:
   an insertion unit configured to be inserted into a guide hole formed in a vertebral bone; and
   an operation unit configured to be connected to the insertion unit, to which vibration is transmitted from the insertion unit, and held by a user, wherein
   the insertion unit comprises:
   a tube member;
   an ultrasonic transducer which is provided at a front end portion of the tube member and configured for inspecting an inside of the vertebral bone by ultrasound diagnosis; and
   a front-end component provided at the front end portion of the tube member, and which comprises a metal member having a tactile member configured for inspecting the inside of the vertebral bone by a tactile sense of the user and an anchor connected to the tactile member, and an insulating member having a surrounding portion that surrounds the anchor is provided between the anchor and the tube member, and
   of the front-end component, an insertion portion made of the anchor and the surrounding portion is fitted into the tube member, wherein
   the tube member is made of a metal pipe member having a shielding function and a vibration transmitting function, and
   the insertion unit further comprises an insulating sheath tube covering an outer side of the tube member.

2. The ultrasonic probe for supporting spine surgery according to claim 1, wherein
   the insertion portion has a circular cylindrical shape, and the anchor has a circular cylindrical shape with a side surface having a detachment-preventing structure.

3. The ultrasonic probe for supporting spine surgery according to claim 2, wherein
   the detachment-preventing structure has at least one recess or projection.

4. The ultrasonic probe for supporting spine surgery according to claim 1, wherein
   the insulating member comprises a cap portion which is connected to the surrounding portion and which covers a front end opening of the tube member, and
   the cap portion and a front end opening of the insulating sheath tube are adhered to each other.

5. The ultrasonic probe for supporting spine surgery according to claim 4, wherein
   the cap portion and the front end opening of the insulating sheath tube are integrated by welding.

6. The ultrasonic probe for supporting spine surgery according to claim 4, wherein
the cap portion has a dome shape swelled in a front direction, and
the tactile member has a shaft which protrudes from a central portion of the cap portion and which is directed in a predetermined direction perpendicular to a central axis of the tube member, and a spherical head provided at a front end portion of the shaft.

7. The ultrasonic probe for supporting spine surgery according to claim 6, wherein
all or a part of the head protrudes toward a living body side in relation to a side surface level of the tube member in the predetermined direction.

8. The ultrasonic probe for supporting spine surgery according to claim 7, wherein
the ultrasonic transducer is an array transducer comprising a plurality of transducer elements,
an opening for allowing passage of ultrasound transmitted from or received by the array transducer in the predetermined direction is formed at the front end portion of the tube member, and
a transducer unit comprising the array transducer is embedded at a deeper side of the opening in the tube member.

9. The ultrasonic probe for supporting spine surgery according to claim 8, wherein
insulating molding is applied around the transducer unit.

10. A method of manufacturing an ultrasonic probe for supporting spine surgery, comprising the steps of:
manufacturing a front-end component comprising a metal member having a tactile member and an anchor connected to the tactile member, and an insulating member having a cap portion and a surrounding portion connected to the cap portion and surrounding the anchor, wherein the insulating member that surrounds the anchor is provided between the anchor and the tube member;
adhering the front-end component and an insulating sheath tube, to manufacture an outer assembly by integrating the cap portion and an opening of the insulating sheath tube by welding;
manufacturing an inner assembly by providing a transducer unit having an ultrasonic transducer in a front end portion of a metal pipe member;
manufacturing an insertion unit by inserting the inner assembly into the outer assembly; and
connecting the insertion unit and an operation unit.

11. The method of manufacturing the ultrasonic probe for supporting spine surgery according to claim 10, wherein
in the step of manufacturing the outer assembly, a circular cylindrical slit is formed between an insertion portion in the front-end component and the insulating sheath tube, and
in the step of manufacturing the insertion unit, the front end portion of the metal pipe member is inserted into the circular cylindrical slit.

12. The method of manufacturing the ultrasonic probe for supporting spine surgery according to claim 10, wherein
in the step of manufacturing the insertion unit, the inner assembly is positioned in the outer assembly such that a direction in which the tactile member points and a direction in which by the ultrasonic transducer points match each other.

13. The method of manufacturing the ultrasonic probe for supporting spine surgery according to claim 10, wherein
in the step of manufacturing the insertion unit, a molding adhesive is applied into the outer assembly before the inner assembly is inserted into the outer assembly.

* * * * *